United States Patent
Hope et al.

(10) Patent No.: US 11,627,907 B2
(45) Date of Patent: Apr. 18, 2023

(54) METHOD AND APPARATUS FOR THE CAPTURE OF INTRA-CELLULAR ACTIVITY

(71) Applicants: Galiana Technology Inc., San Diego, CA (US); National Institutes of Health, Office of Technology Transfer, Rockville, MD (US)

(72) Inventors: Bruce T Hope, Ellicott City, MD (US); Mark A Wells, San Diego, CA (US); Gregory D Sutton, Del Mar, CA (US)

(73) Assignees: National Institutes of Health, Office of Technology Transfer, Rockville, MD (US); Galiana Technology Inc., San Diego, CA (US)

( * ) Notice: Subject to any disclaimer, the term of this patent is extended or adjusted under 35 U.S.C. 154(b) by 849 days.

(21) Appl. No.: 16/450,895

(22) Filed: Jun. 24, 2019

(65) Prior Publication Data

US 2020/0146610 A1    May 14, 2020

Related U.S. Application Data

(63) Continuation of application No. 14/834,334, filed on Aug. 24, 2015, now abandoned.
(Continued)

(51) Int. Cl.
*A61B 5/00* (2006.01)
*A61B 5/145* (2006.01)
(Continued)

(52) U.S. Cl.
CPC .......... *A61B 5/4064* (2013.01); *A61B 5/0031* (2013.01); *A61B 5/076* (2013.01);
(Continued)

(58) Field of Classification Search
CPC ..... A61B 5/4064; A61B 5/0031; A61B 5/076; A61B 5/14546; A61B 5/1473;
(Continued)

(56) References Cited

U.S. PATENT DOCUMENTS

| | | | |
|---|---|---|---|
| 2012/0034622 A1* | 2/2012 | Ignatius | B82Y 5/00 435/7.2 |
| 2014/0357964 A1* | 12/2014 | Wisniewski | A61B 5/742 600/595 |

OTHER PUBLICATIONS

Adam H. Marblestone, Physical principles for scalable neural recording, Oct. 21, 2013, Frontiers in Computational Neuroscience, 7, pp. 1-34 (Year: 2013).*

(Continued)

*Primary Examiner* — Erin M Piateski
(74) *Attorney, Agent, or Firm* — Kaplan IP Law, PLLC; Jonathan T. Kaplan

(57) ABSTRACT

An intracellular monitoring device (IMD) that fits completely inside a living cell, and causes no significant impairment, to a cell's normal biological processes. The IMD monitors a cell for its level of a biological substance (e.g., calcium ion concentration) of interest. If the biological substance reaches or exceeds a threshold, the IMD transmits an electromagnetic signal, received by an antenna outside the cell. Each IMD has its electromagnetic signal encoded with a unique frequency. Detection of the frequency components, in the signals received by an antenna, permits identification of the source IMD's. A high calcium ion concentration is indicative of a strongly-activated cerebral cortex neuron. Brain tissue is relatively transparent to near infrared, making it a good frequency band, for the electromagnetic signals from neuron-monitoring IMD's. The near infrared of each IMD can be produced by quantum dots, powered by bioelectric catalysis triggered by high calcium ion concentration.

8 Claims, 24 Drawing Sheets

Related U.S. Application Data

(60) Provisional application No. 62/041,028, filed on Aug. 23, 2014.

(51) Int. Cl.
*A61B 5/1473* (2006.01)
*A61B 5/07* (2006.01)

(52) U.S. Cl.
CPC ........ *A61B 5/1473* (2013.01); *A61B 5/14546* (2013.01); *A61B 5/6868* (2013.01); *A61B 2560/0204* (2013.01); *A61B 2562/028* (2013.01); *A61B 2562/0285* (2013.01); *Y10S 977/774* (2013.01)

(58) Field of Classification Search
CPC .......... A61B 5/6868; A61B 2560/0204; A61B 2562/028; A61B 2562/0285; Y10S 977/774
USPC .................................. 257/E29.071
See application file for complete search history.

(56) References Cited

OTHER PUBLICATIONS

Alberto Curto, Unidirectional Emission of a Quantum Dot Coupled to a Nanoantenna, Aug. 20, 2010, Science, 329(5994), pp. 930-933 (Year: 2010).*

* cited by examiner

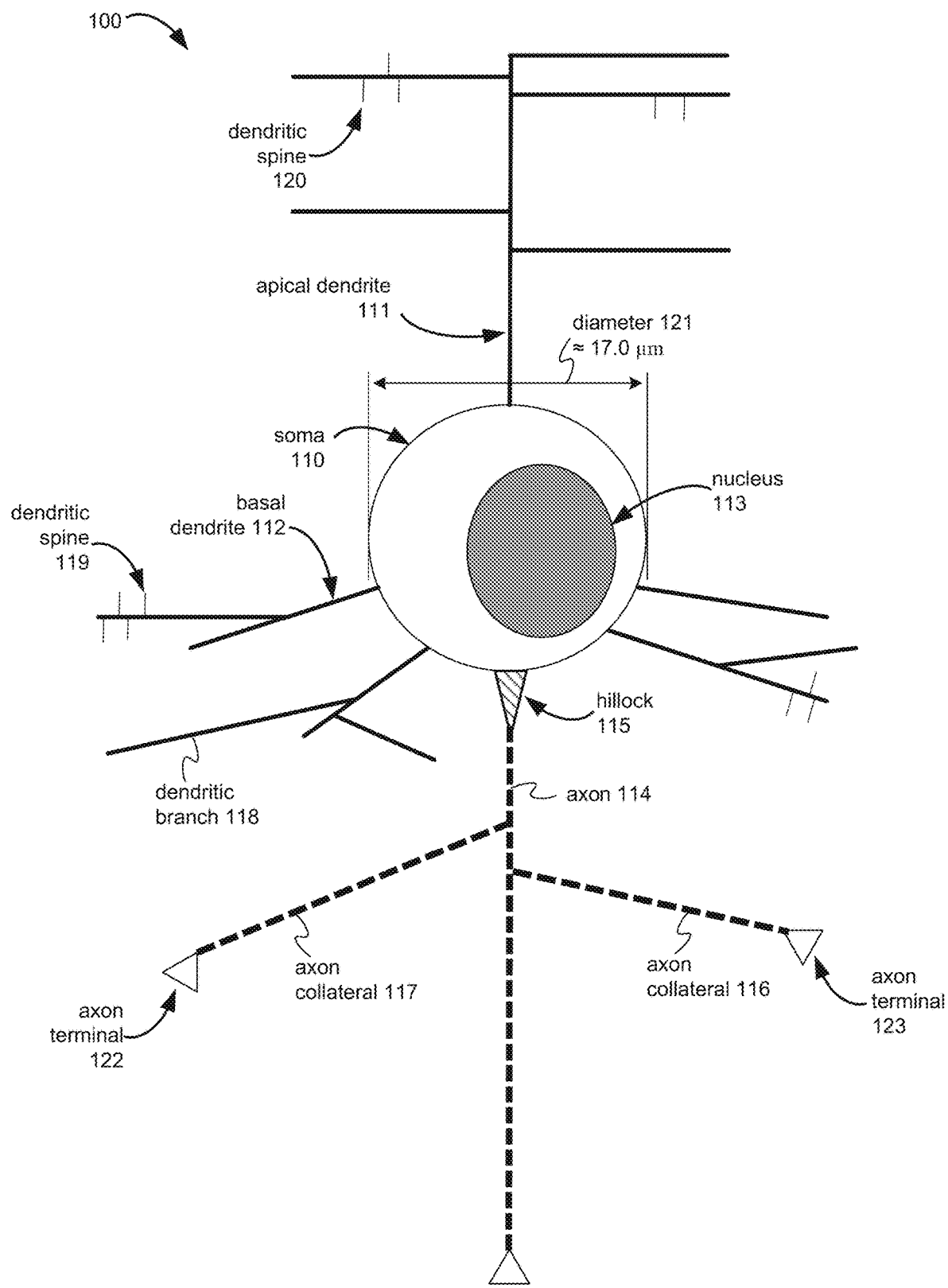

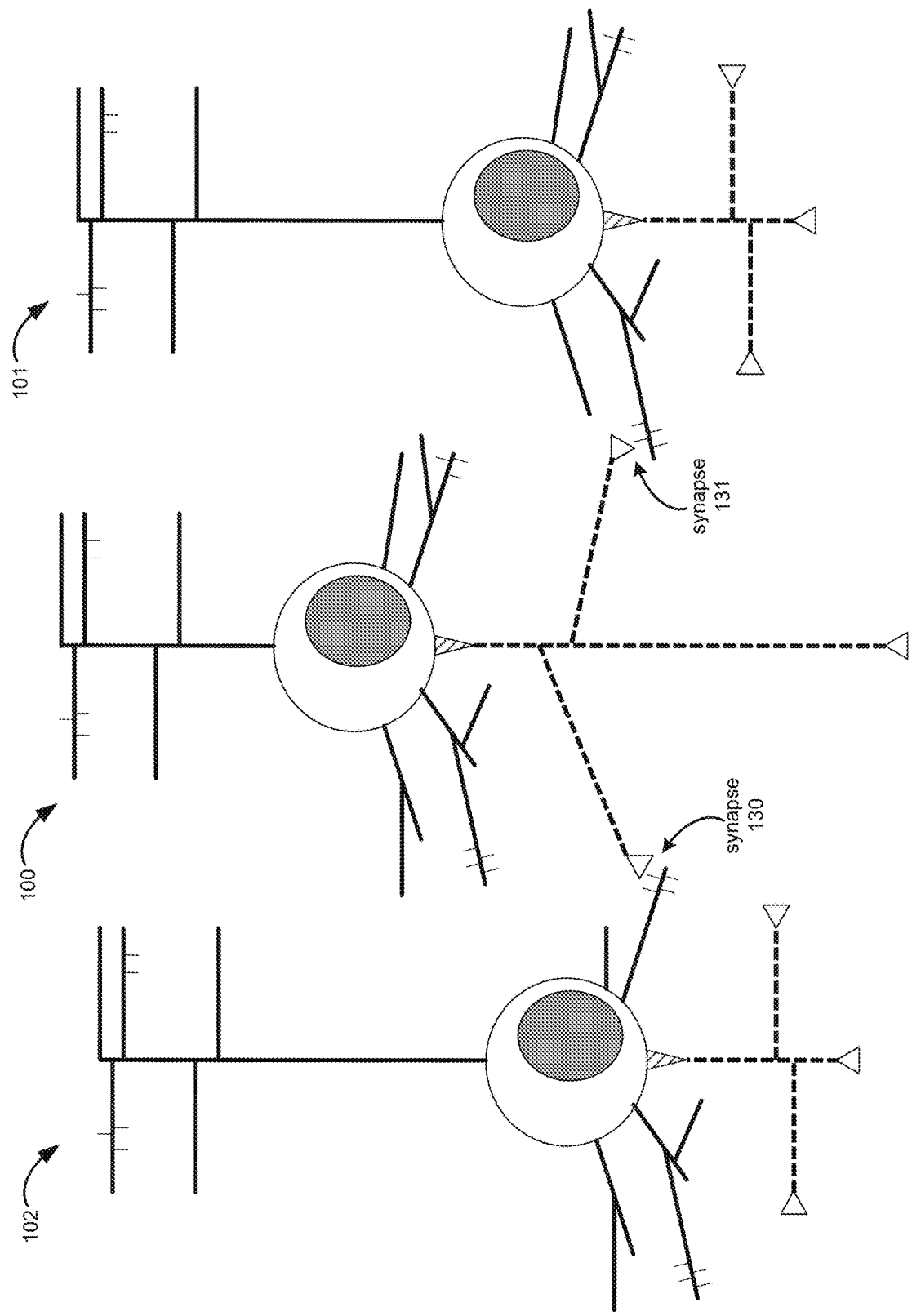

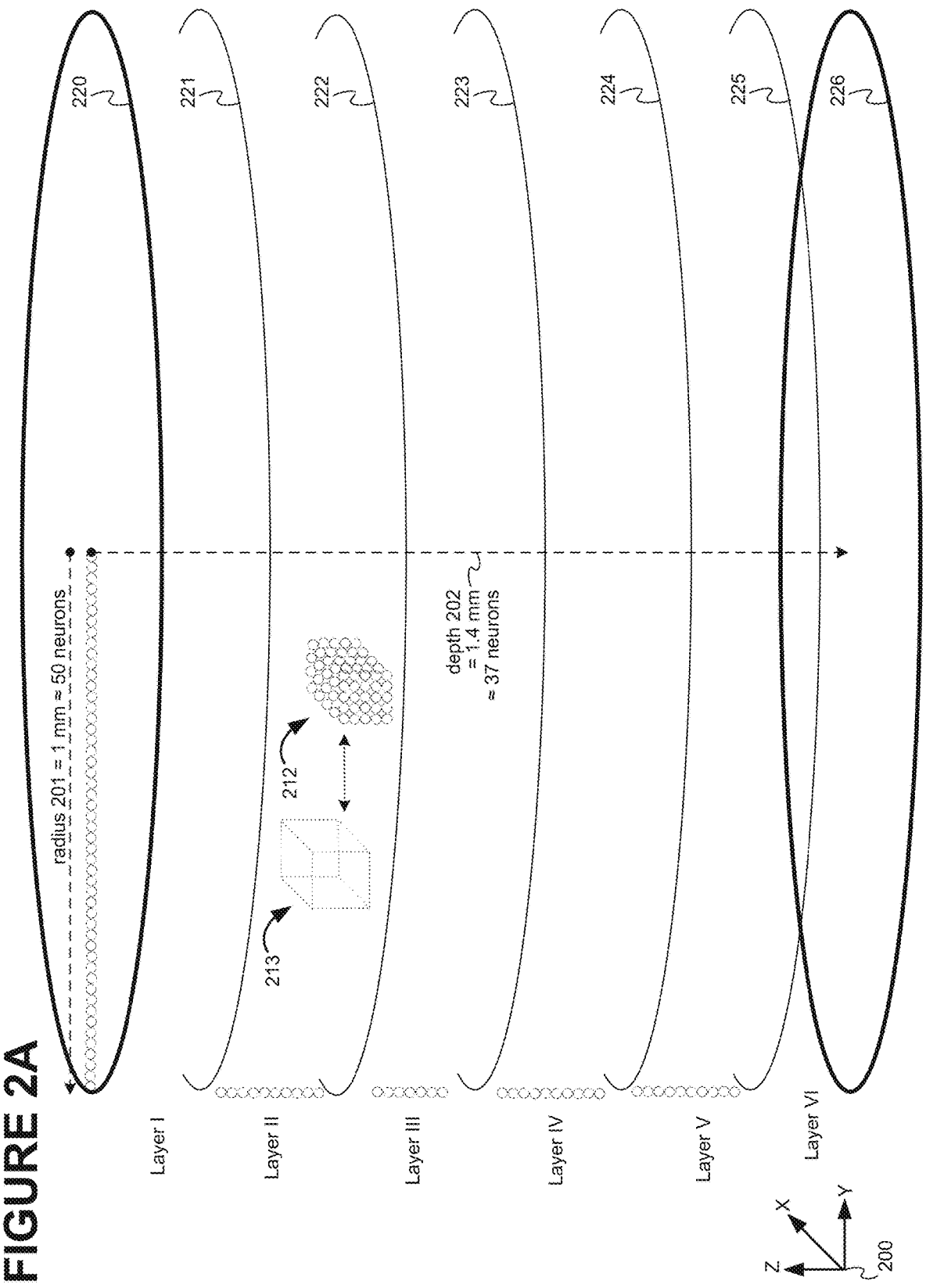

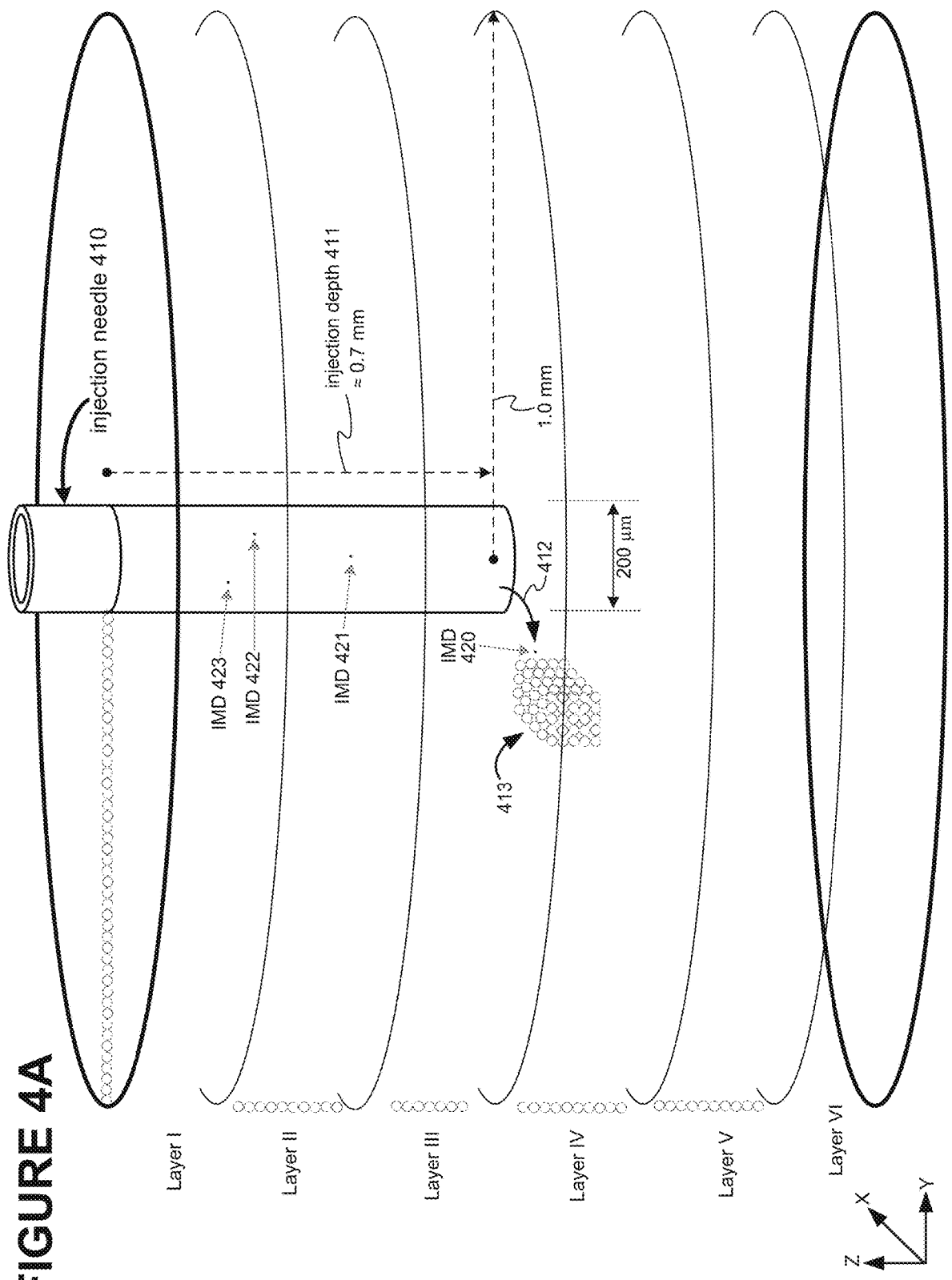

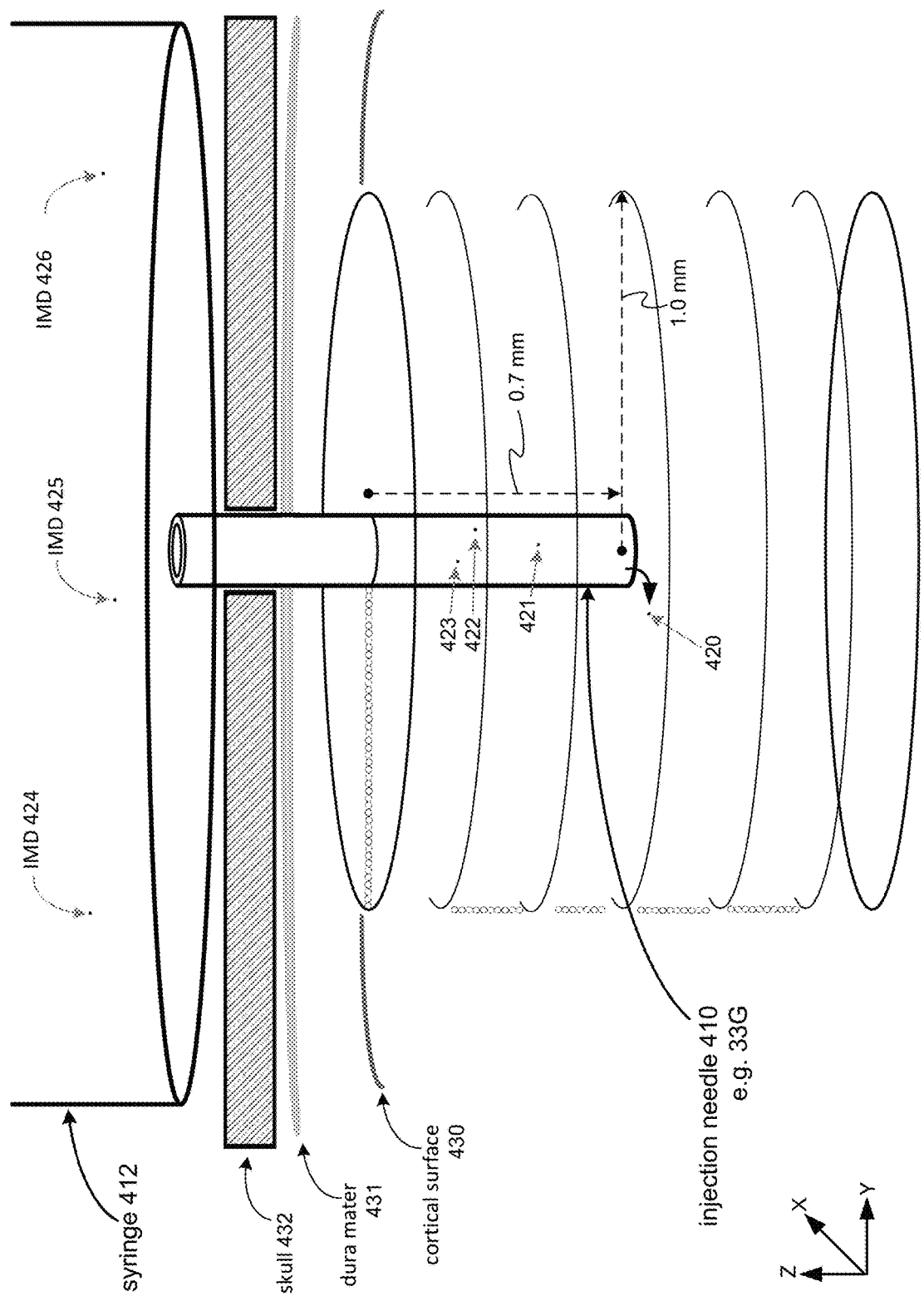

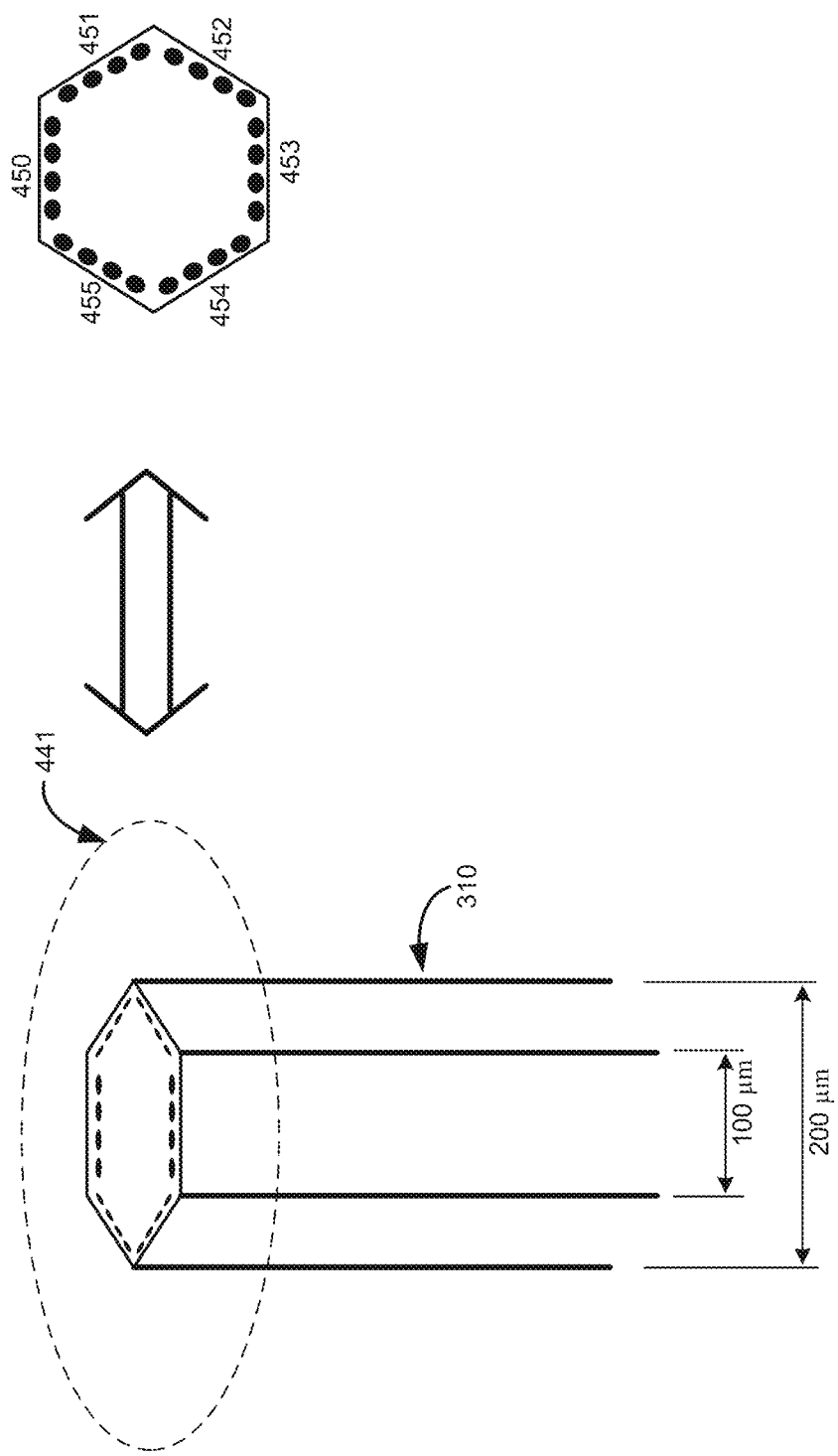

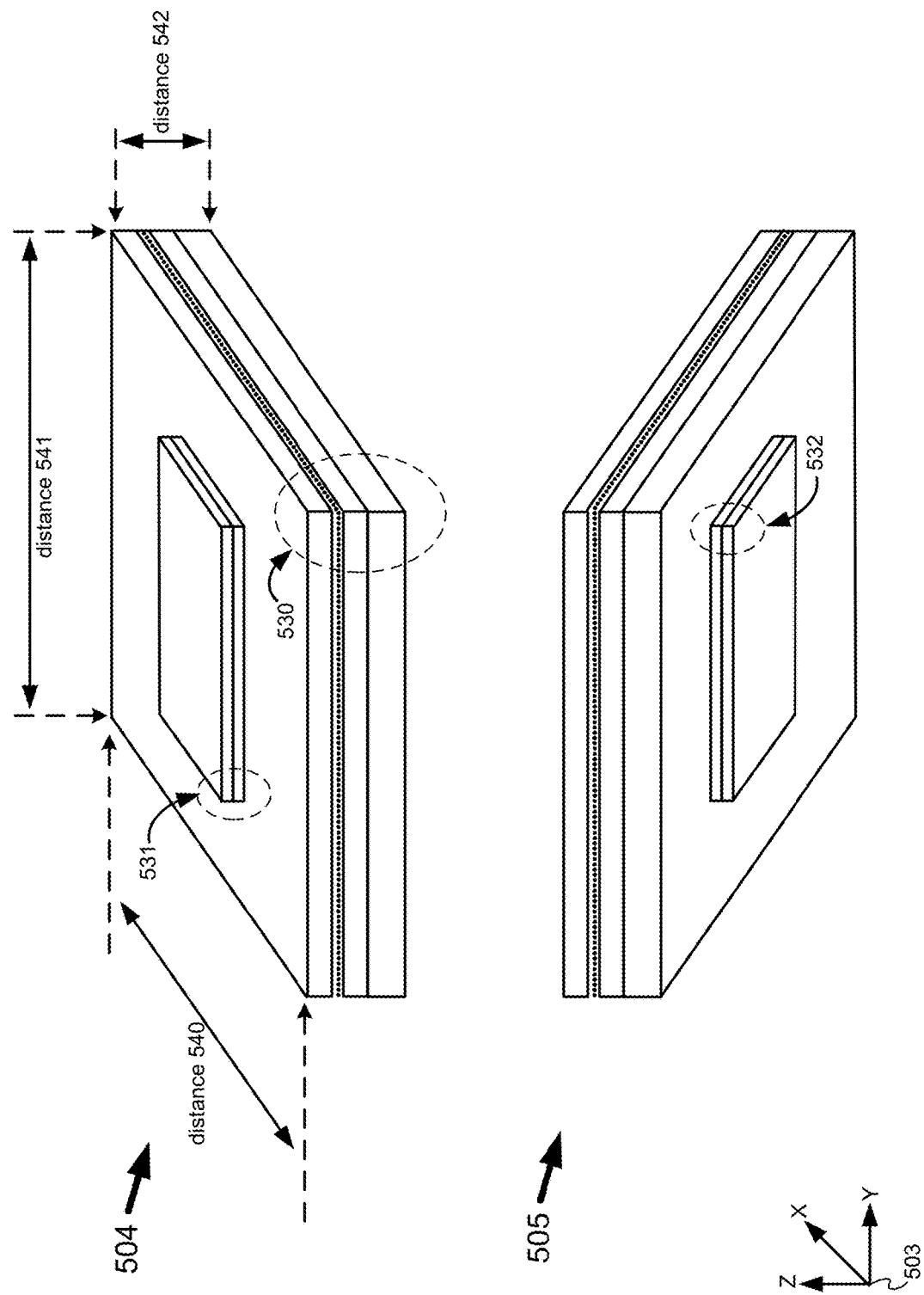

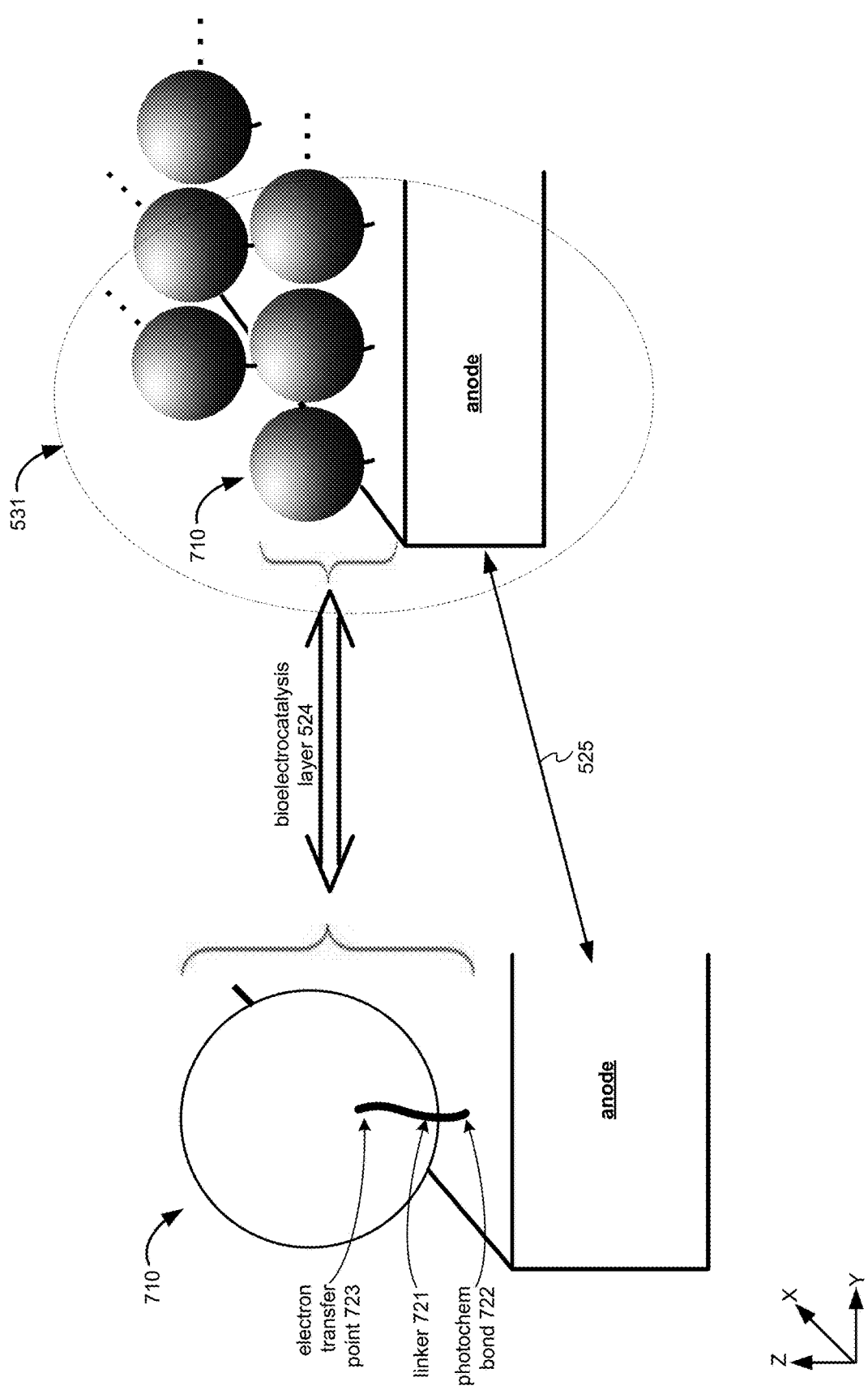

METHOD AND APPARATUS FOR THE CAPTURE OF INTRA-CELLULAR ACTIVITY

As provided for under 35 U.S.C. § 120, this patent claims benefit of the filing date of the following U.S. patent application, herein incorporated by reference in its entirety: "Method and Apparatus for the Capture of Intra-cellular Activity," filed 2015 Aug. 24 (y/m/d), having inventor Bruce T. Hope, Mark A. Wells, and Gregory D. Sutton, and application Ser. No. 14/834,334.

As provided for under 35 U.S.C. § 119(e), application Ser. No. 14/834,334 claims benefit of the filing date for the following U.S. provisional patent application, herein incorporated by reference in its entirety:

"Method and Apparatus for the Capture of Intra-cellular Activity," Application No. 62/041,028, Confirmation No. 1510, and filed 2014 Aug. 23 (y/m/d).

FIELD OF THE INVENTION

The present invention relates generally to capturing cellular activity, and, more particularly, to capturing intracellular activity with a monitoring device, the monitoring device implanted in each cell to be monitored.

BACKGROUND OF THE INVENTION

The chemical and electrical processes inside living cells are known to be extremely complicated, and existing techniques for collection of information on such processes, with sensing apparatus external to the cell, are known to have a variety of significant limitations.

It would therefore be desirable to be able to develop new mechanisms by which cellular activity can be monitored.

An example area, where new mechanisms for sensing are particularly desirable, is the monitoring of neural activity.

Each existing technique, for the capture of neural-activity, fits into one of the two following categories:
1. Captures the activity of a large region cortical manner, each region including at least hundreds of thousands of neurons, but the activity of individual neurons, within a monitored region, is unknown. An example technique in this category is functional magnetic resonance imaging.
2. Captures the activity of individual neurons, but only a small number of adjacent neurons (e.g., on the order of 100) can be simultaneously monitored. Example techniques in this category include electrode arrays and calcium imaging.

It would therefore be desirable to have neuronal-activity monitoring systems that capture both the activity of a large area of neurons and, within that area, activity on an individual-neuron level.

BRIEF DESCRIPTION OF THE DRAWINGS

The accompanying drawings, that are incorporated in and constitute a part of this specification, illustrate several embodiments of the invention and, together with the description, serve to explain the principles of the invention:

FIG. 1A presents an idealized and simplified pyramidal neuron, as can be found in a mammalian cerebral cortex.

FIG. 1B shows the neuron from FIG. 1A providing an output to each of two neighboring pyramidal neurons.

FIG. 2A presents an example volume of cortical tissue, from a simplified and idealized region of the cerebral cortex of a laboratory rat.

FIG. 4A depicts a section of cortical tissue identical to that of FIG. 3A, except that, rather than an antenna structure 310, an injection needle 410 is shown as having been inserted.

FIG. 4B is similar to FIG. 4A, except it shows a syringe structure, as well as additional types of tissue, for purposes of providing further context to the injection process.

FIG. 4D depicts views of the top of antenna 310, labeling its six sides and illustrating the exiting optical fibers.

FIG. 5B shows the same two views as are depicted in FIG. 5A, except dimensions and regions are labeled.

FIG. 7A is a highly magnified view of region 531, as indicated in FIG. 5B, that shows individual catalyst and linker molecules.

DETAILED DESCRIPTION OF PREFERRED EMBODIMENTS

Figure 1C:
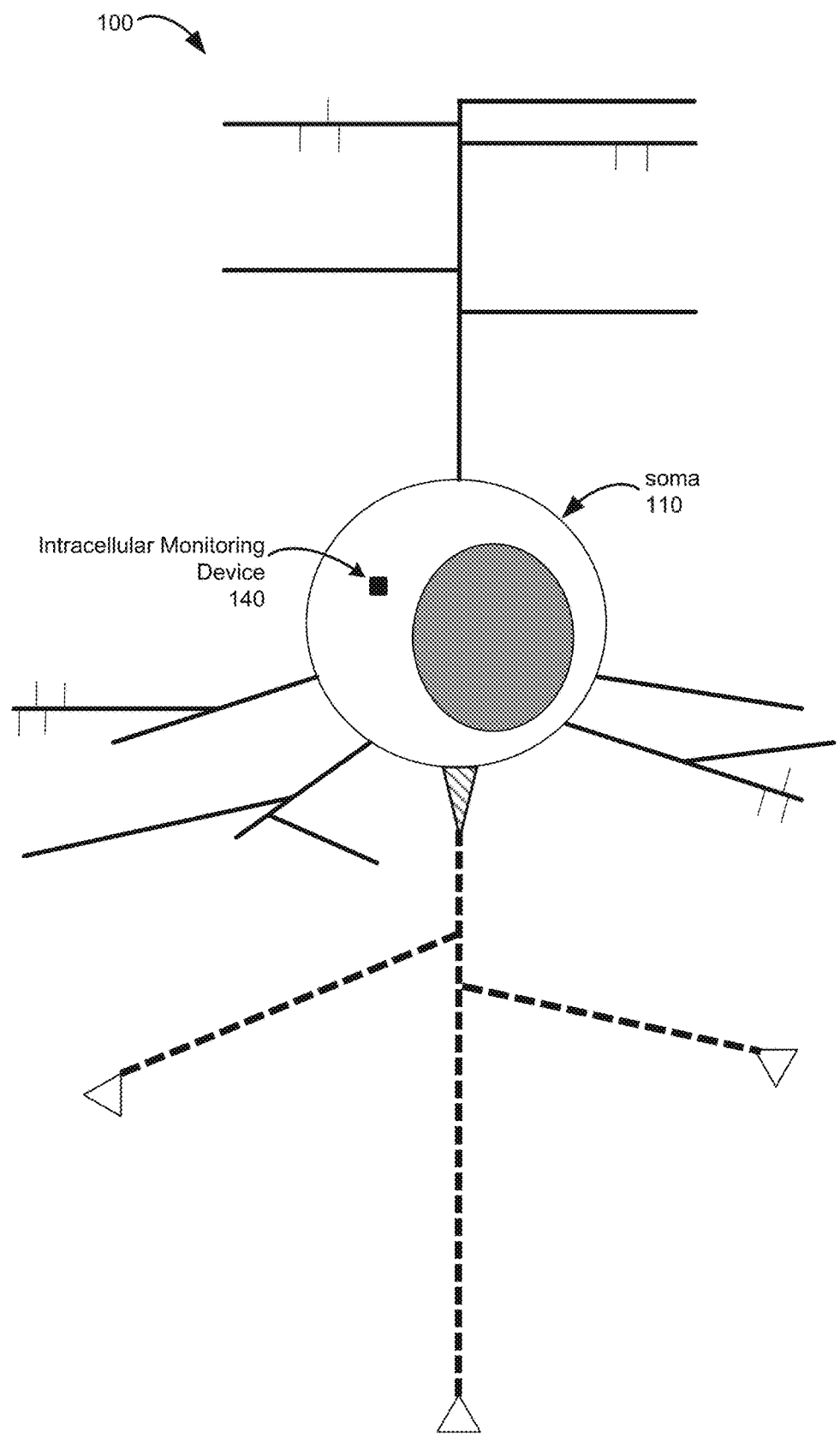
FIG. 1C shows the same neuron of FIG. 1A, except it includes an intracellular monitoring device.

Reference will now be made in detail to various embodiments of the invention, examples of which are illustrated in the accompanying drawings. Wherever possible, the same reference numbers will be used throughout the drawings to refer to the same or like parts.

Please refer to Section 10 ("Glossary of Selected Terms") for the definition of selected terms used below.

TABLE OF CONTENTS TO DETAILED DESCRIPTION

1 Overview
2 Pyramidal Neurons
3 IMD Overview
4 Cerebral Cortex Layers
5 Antenna Structure
6 Injection Process
7 EM Collection
8 IMD, Example Construction
   8.1 Overview
   8.2 Quantum Dot LED
   8.3 Substrate and Metal Layers
   8.4 Bioelectrocatalysis
      8.4.1 Overview
      8.4.2 Molecular Level
   8.5 Endocytosis
   8.6 Inert Coating
9 Computing Equipment
10 Glossary of Selected Terms

1 Overview

Recent research indicates that, within at least higher-order organisms (e.g., the scientific class Mammalia, more commonly known as mammals), it would be desirable to be able to accomplish the following:

Across a volume of cortical-matter large enough to include, at least, thousands of active neurons, an ability to individually monitor the activity of a large number of those neurons (e.g., at least hundreds of neurons).

We shall refer to this kind of monitoring capability as "Large Scale Fine Grained" neural monitoring (also referred to herein as "LSFG monitoring"). LSFG monitoring has many important areas of application, including the following two: development of brain-machine interfaces, and cognitive neuroscience research. Regarding the latter, there is an area of research based on the organizing principal of "neuronal ensembles" (also referred to herein as "neuronal ensemble research"). An overview of neuronal ensemble research can be found in the following publication, herein incorporated by reference in its entirety:

"New technologies for examining the role of neuronal ensembles in drug addiction and fear," by Cruz et al., in Nature Reviews Neuroscience, Volume 14, November 2013, 12 pages ("the Cruz et al. paper").

Neuronal ensemble research has been useful, for example, in better understanding higher-level cognitive activities, such as a mammal's ability to distinguish the "place" where it is currently located, compared to places (or living environments) where the animal has been previously. An example of this kind of learning, covered in the Cruz et al. paper, is the ability to train a laboratory rat to recognize where it is placed. The rat learns that when it is in a first cage, with a first set of environmental queues, it is able to obtain a food or drug reward upon pressing a lever. The rat is also taught that when it has been placed in a second cage, with a second and different set of environmental queues, pressing a similar lever will produce no reward. A study discussed in the Cruz et al. paper proved that the cognitive processes of the rat, that enable it to remember one environment as different from another, involve neural ensembles.

A neuronal ensemble can be defined as follows:

Within a cortical-area comprising at least thousands of neurons, an ensemble is said to occur when, and only when, a small percentage of those neurons is strongly activated.

A small percentage is a percentage within the range of approximately 1 to approximately 5%.

As an approximate, and representative, value, a neuron is strongly activated when it consistently produces (e.g., over a period of approximately one second or more) pulses at a rate of about 10 Hz. An approximate and representative duty cycle, when generating 10 Hz, is as follows: for each cycle, approximately 10% of the time (e.g., 10 ms) is consumed producing the pulse (also called the "action potential") and 90% of the time (e.g., 90 ms) is consumed by the neuron's polarization being decreased, as the neuron prepares to produce a next strong-activation pulse.

The Cruz et al. paper showed that a rat's memory of being in the first cage is embodied in a first ensemble, and its memory of being in the second cage is embodied in a second ensemble. The study showed that the two ensembles are different from each other.

The present invention is based upon a realization that microelectronics has advanced to a point where it is now possible to implant a monitoring device, referred to herein as an "Intracellular Monitoring Device" (or IMD), entirely within a living cell. This monitoring device can be made small enough such that it causes, at most, insignificant impairment to the normal biological processes of the cell in which it is implanted. Thus, while a cell is undergoing its normal biological processes, an IMD can sense one or more conditions in the cell, and wirelessly transmit the collected information to one or more receivers placed externally to the cell.

The IMD can be implanted within a single cell organism, or, for any type of multi-cellular organism, within the cells of any of its tissue types.

For Mammalia, cells typically range in diameter from about 10-50 μm. A rectangular, box-shaped, IMD, with no edge having a dimension greater than 1.0 μm, can be expected to be implantable within any mammalian cell within the typical size range.

The example cell type focused-upon herein is the neuron and, more particularly, the pyramidal neurons of the mammalian cerebral cortex. Such cells typically have a cell body (or soma) with a diameter ranging from 10-20 μm. An example animal addressed herein is the laboratory rat where, as a simplified approximation, the cell body of its pyramidal neurons are assumed to have a diameter of 17 μm.

2 Pyramidal Neurons

This section presents a basic overview, of an idealized and simplified pyramidal neuron, as can be found in a mammalian cerebral cortex (depicted in FIG. 1A). This overview, and the next section's overview of cortex layers, are presented for purposes of assuring appropriate context, for application of the present invention. There is a vast scientific literature on the structure of neurons and the cerebral cortex, and such literature can be consulted, as necessary, for a particular application of the invention. Similarly, the present invention can be applied to the monitoring of intracellular activity in other types of cells, by consulting the appropriate scientific and/or medical literature.

While there are many other types of cells within a mammalian brain, the focus of the present example is on the pyramidal neurons, as these are the focus of neuronal ensemble research, as discussed above.

The main cell body of a neuron (e.g., neuron 100 of FIG. 1A) is called the soma (such as soma 110 of FIG. 1A). As can be seen in the figure, example soma 110 is approximated as a sphere, with its diameter labeled 121. Diameter 121 is shown as being 17 μm, used herein as an average, representative value, for the laboratory rat. While an actual soma would contain many other organelles, for purposes of simplicity of exposition, only the nucleus (nucleus 113) is shown for soma 110.

As is well understood in the scientific literature, a neuron receives input signals through its dendrites and sends out output signals through its axons. A synapse is a region where the axon of one neuron sends a signal to the dendrite of another neuron.

A pyramidal neuron is characterized by having two main types of dendrites:

Basal dendrites (such as basal dendrite 112), that, in general, extend laterally from the soma. Taken together, the lateral directions of the basal dendrites can be summarized as defining a kind of plane, relative to a neuron's soma.

An apical dendrite (such as apical dendrite 111), that extends in a direction that is, in general, perpendicular to the plane defined by the basal dendrites. An apical dendrite is often quite long, and typically crosses through other "layers" of neurons (the six main layers, of cerebral cortex pyramidal neurons, are presented below).

Each basal dendrite can have one or more branches, such as dendritic branch 118 of FIG. 1A. The apical dendrite also has, in general, one or more dendritic branches.

When a neuron "decides" (as a result of receiving sufficient inputs at its dendrites) to output a signal, the signal begins at the neuron's hillock (such as hillock 115). The signal travels away from the neuron's soma via its axon, and axon branches (an axon branch is referred to as a "collateral," such as collaterals 116 and 117 of FIG. 1A). The traversal of a signal, along a neuron's axon, is referred to as an "action potential." An action potential "moves" as a result of a kind of rolling wave of depolarization, followed by re-polarization, in an electrochemical process.

FIG. 1B shows another copy of neuron 100 (from FIG. 1A), but now neuron 100 is shown as providing an output to two neighboring pyramidal neurons: neuron 102 and neuron 101. A connection, from an output of neuron 100 to an input of neuron 102, is indicated as a synapse 130 in FIG. 1B. Similarly, a connection, from an output of neuron 100 to an input of neuron 101, is indicated as a synapse 131 in FIG. 1B. The side of synapse 130 formed by neuron 100 is indicated in FIG. 1A as axon terminal 122. Similarly, the side of synapse 131 formed by neuron 100 is indicated in FIG. 1A as axon terminal 123. Each of neurons 102 and 101 forms its side of, respectively, synapse 130 and 131, from the dendritic spine that is, respectively, closest to axon terminal 122 or 123. In general, a dendritic spine is a spike-shaped structure that is, relative to the length of the dendrite to which it is attached, quite small. An example dendritic spine 120, for neuron 100, is indicated in FIG. 1A.

As is well known, the axon terminal side of a synapse emits molecules of a chemical called a neurotransmitter. The neurotransmitter molecules are received by the dendritic spine, on the receiving side of a synapse.

3 IMD Overview

FIG. 1C depicts another copy of neuron 100 (already discussed above with respect to FIGS. 1A and 1B), but in FIG. 1C neuron 100 is shown as containing an Intracellular Monitoring Device (or "IMD"), labeled 140.

An IMD, as described herein, includes at least the following characteristics:

1. The IMD is small enough such that it can fit entirely inside a living cell, while causing, at most, insignificant impairment to the cell's normal biological processes. To accomplish this, the longest dimension of an IMD is typically limited to being no more than approximately 1 μm. FIG. 1C is intended to show relative scale, between IMD 140 and soma 110, where IMD 140 is a 1 μm square (and, as stated above, soma 110 has a 17 μm diameter).
  2. The IMD collects data, regarding at least one biological process of the cell in which it is contained (hence, it is an intracellular monitoring device).
  3. The IMD transmits an electromagnetic (or EM) signal, that is both indicative of the particular IMD from which it originates, and that also communicates information, regarding the at least one biological process it has been monitoring.

When used as part of a system for intracellular monitoring, an antenna is placed sufficiently close to the IMD, such that the IMD's EM signal can be received, and then analyzed for its informational content.

For an IMD to be "entirely inside a living cell" means that the IMD is completely within the cell membrane (also called a plasma membrane or cytoplasmic membrane) of the cell it is to monitor. Being completely inside a cell is compatible with an IMD being in contact with the cell membrane, just so long as this contact is with the interior wall of the cell membrane.

Further aspects, of IMD design, can include the following:

Selection of its EM spectrum for transmission:
    Depending upon the type of living tissue, whose cells are to be monitored, a suitable "wavelength window" can be determined. This is a range of spectrum for which the relevant tissue presents minimal attenuation, or, at least, an acceptable level of attenuation.
    With regard to cortical brain tissue, measurements have shown that it is most transparent to that portion of the EM spectrum called "Near-Infrared" (or NIR). For this reason, when applied to the monitoring of cortical neurons, a preferred embodiment of IMD uses NIR to transmit its information. More specifically, NIR that is approximately within the following range of wavelengths is preferred: 700 nm-1100 nm. To show how important the correct choice of spectrum can be, the below table summarizes the difference in attenuation, between use of the visible light or NIR:

| Tissue traversed | Attenuation of Visible | Attenuation of NIR |
| --- | --- | --- |
| 1 mm | 64%-99% | 14% |
| 1 cm | 99.9996% | 64% |

As can be seen, even after passing through 1 cm of cortical tissue, NIR is attenuated by only 64%. In comparison, over the same distance, the visible spectrum is attenuated 99.9996%.

Selection of a device for generating the IMD's EM transmission, and a technique by which the particular IMD, that is the source of a particular EM transmission, can be identified:

With regard to the production of NIR radiation, quantum dots are a suitable technology.

Because a quantum dot can be precisely tuned, regarding the frequency of NIR it emits, it is also a good technology for encoding, in the EM transmission, the identity of the particular IMD that is the transmission's source. For example, all the quantum dots for each IMD can be tuned to a specific and unique frequency—it is only necessary that all the quantum dots of an IMD have the same diameter. In this way, 100's of different QD-LED's can be produced, each with its own unique and precisely-tuned frequency.

NIR Light-Emitting Diodes (LED's) can be used as the EM source for an IMD. However, NIR LED's are, in general, available in a smaller variety of different frequencies and/or more difficult to precisely tune to a particular frequency. This makes it difficult to separately monitor 100's of IMD's by simply assigning each its own frequency within the NIR band (see Section 7 "EM Collection").

Selection of the biological processes to be monitored, and the techniques for capturing the information:

With regard to cortical brain tissue, and, more particularly, the detection of ensembles, it has been determined that a high concentration of calcium ions, in a neuron's soma, is a reliable indicator of whether that neuron is strongly activated. This means that a neuron, during the period of time when it is strongly activated and is actually producing a pulse, its calcium level is high. During its period of decreasing polarization, when the strongly-activated neuron is preparing for production of a next pulse, its calcium ion concentration initially starts out low. At, or shortly before, the point in time when depolarization is sufficient to cause the neuron to "fire" (i.e., produce an action potential), the calcium ion concentration reaches its approximately maximal levels An example technique, for causing an IMD to detect the high calcium levels associated with strong activation, is called bioelectrocatalysis. More specifically, an IMD can be equipped with an enzyme. The enzyme enables production of an electric current only when a threshold calcium level, corresponding to strong activation of a neuron, is reached. Utilization of this calcium-dependent electric current, to trigger a coded NIR transmission by an IMD, can be accomplished with any suitable technique. An example technique, covered in more detail in a following section, is to use this calcium-dependent electric current as part of the main power supply of an IMD. Thus, when the calcium-dependent electric current is being produced for an IMD, that IMD is "powered-up." An IMD can be designed so that, as long as it has power, it continuously transmits a particular frequency of NIR radiation.

Providing power for the IMD. As discussed above, this can be provided by bioelectrocatalysis, with the beginning of the bioelectrocatalysis also being a signal, indicating that the monitored biological process has reached a threshold of interest. Alternatively, or in addition, an IMD can be powered by EM radiation it is designed to receive. For example, the IMD can contain a dipole antenna, for receipt of such broadcast power.

4 Cerebral Cortex Layers

As discussed above, for purposes of neuronal ensemble research, it would be extremely useful to have the ability to accomplish LSFG monitoring of cortical tissue. FIG. 2A presents an example appropriate volume of cortical tissue, from a simplified and idealized region of the cerebral cortex of a laboratory rat. FIG. 2A depicts a cylindrical volume, with a depth 202 and a radius 201. Depth 202 is the full depth of the cerebral cortex. Depth 202 is 1.4 mm, used as an average, representative value, for the laboratory rat. Radius 201 is chosen to be 1.0 mm. (In FIG. 2A, radius 201 is represented by a 10 cm distance, and thus the figure represents an approximately 100× magnification, of the actual cortical distances.) The cylindrical volume is contained within upper circle 220 and lower circle 226, where 220 represents the cortical surface (e.g., the layer of cortex closest to the skull).

It is standard nomenclature to divide the cerebral cortex, along its depth dimension, into six different layers of pyramidal neurons, numbered I to VI (see left side of FIG. 2A, for this numbering of layers). The six layers are divided from one another, in the figure, by circles 221-225 (the circles representing a simplification and idealization, for purposes of exposition, of the clarity of division between layers). The correspondence, between a neural layer and a pair of labeled circles, is as follows:

Layer I: between 220, and 221.
Layer II: between 221, and 222.
Layer III: between 222, and 223.
Layer IV: between 223, and 224.
Layer V: between 224, and 225.
Layer VI: between 225, and 226.

Per the following estimations, it will be shown that just the small cylindrical region of FIG. 2A (diameter 2.0 mm, depth 1.4 mm) contains approximately $3.0 \times 10^5$ neurons.

First, along the X-Y plane (as indicated by set of axes 200), pyramidal neurons are generally packed quite tightly together. Thus, along a radius of 1.0 mm, one can expect approximately 50 neuron somas. To suggest this density of packing, a line of approximately 50 somas is shown, in FIG. 2A, just below radius 201.

Along depth 202 (the Z axis, as indicated by axes 200), are shown 37 neurons (where 37 is used as an average, representative, value). To suggest the way in which the density of these 37 neurons can be expected to vary, across the layers, the left side of FIG. 2A shows a column of 37 neuronal somas. As can be seen, all 37 somas are shown as being in layers II to V. This is because layers I and VI are used almost entirely to provide space for inter-neuron "wiring." Among layers II to V, layer III is indicated as having 7 neurons along its depth (as an average, representative, value), while each of layers II, IV, and V, is indicated as having 10 neuron somas. This difference is due to the fact that, generally, layer III has fewer neurons, than are present in layers II, IV, and V.

Figure 2B:
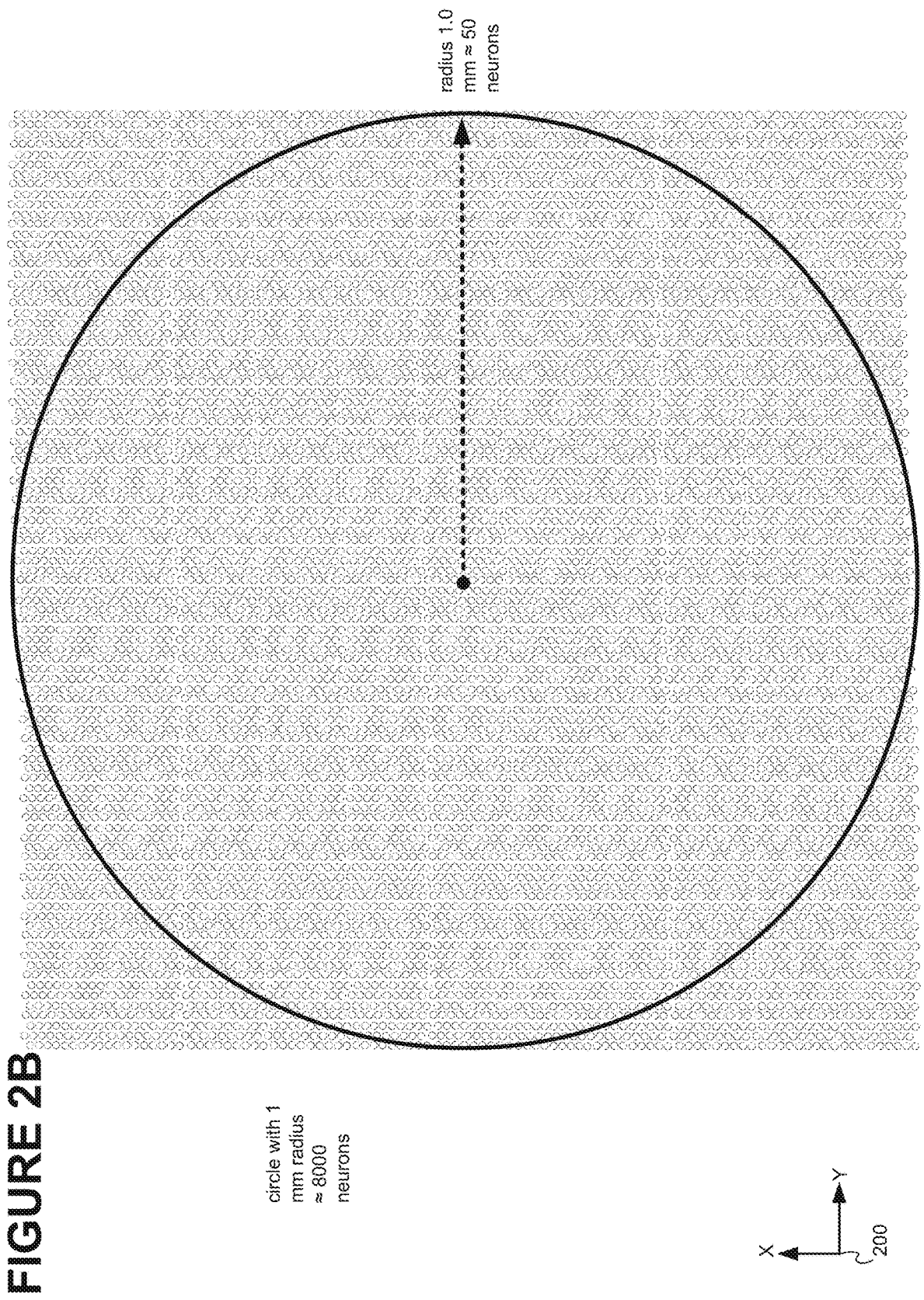
FIG. 2B presents same volume of cortical tissue as FIG. 2A, except shown from a top view.

Given the densities presented in the prior two paragraphs, the total number of neurons, in the cylindrical area of FIG. 2A, can be estimated. First, the number of neurons for each circular area, where that circular area has only one neuron along its depth, can be found by application of the formula: Area=$\pi r^2$. Using 50 as the value for r, we find that there are approximately 8000 neurons, in each circular "slice" of the cylinder. A top view of an example circular slice of cortex, along the X-Y plane, is shown in FIG. 2B. This figure depicts approximately 8000 somas, within a circle drawn at scale of approximately 100×. Second, the total number of neurons, expected to be found in the cylindrical area, is then found by simply multiplying the value for a circle (8000) by the total number of such circles expected, along depth dimension 202 (corresponding to the Z axis):

$(8\times10^3)\times(37\times10^0)=296\times10^3$ (i.e., about 300K neurons)

Although FIG. 2A is drawn as mostly empty space, the actual cortical volume it represents is packed, quite densely, with neuron somas. To assist the viewer with imagining this density, a cubic area 212 is shown. Cubic area 212 is drawn as having approximately 5 somas, along all three dimensions, with each dimension of the cube being, approximately, 100 μm. To more clearly represent its shape, cubic area 212 is shown as corresponding to a cube outline 213.

5 Antenna Structure

Any suitable antenna structure can be used, depending upon such factors as:
 The portion of EM spectrum utilized by the IMD.
 The type of tissue to be monitored.
 The environmental situation, in which the complete monitoring system is operating.

Figure 3A:
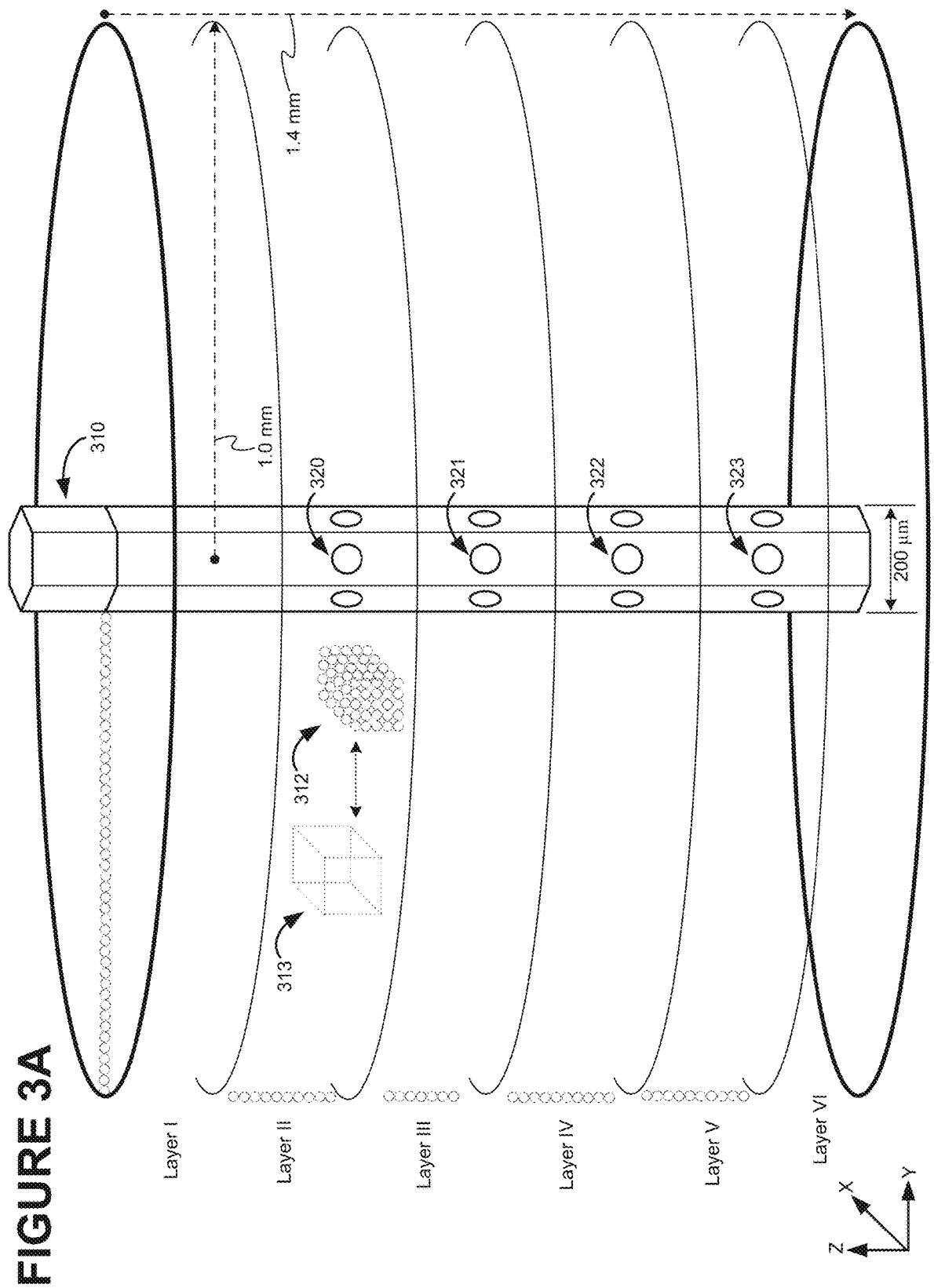
FIG. 3A depicts the same cortical volume depicted in FIG. 2A, except an example antenna 310 is inserted into the cortical tissue.

FIG. 3A depicts the same cortical volume depicted in FIG. 2A, except an example antenna 310 is inserted into the cortical tissue. Antenna 310 is designed under the assumption that the IMD's, whose signals the antenna is designed to receive, are transmitting in the NIR part of the spectrum. The antenna is shown as a hexagonal structure, with a diameter of about 200 μm. For each of the six sides, there are shown four points for collection of EM radiation: one collection point for each of layers II to V. A close-up depiction of the top of antenna 310 is shown in FIG. 4D. Proceeding in a clockwise fashion, from the side farthest from the viewer of FIG. 3A, these sides are numbered: 450-455. For FIG. 3A, only three sides, of hexagonal antenna 310, are visible (corresponding to sides 452-454). Among the three visible sides, the middle side (453) has its EM collection points labeled: 320-323. While antenna 310 is shown as having six sides, any number of sides, suitable for the particular application, can be used. Furthermore, while only four collection points per side are shown, any number of EM collection points, suitable for the particular application, can be used.

Figure 3B:
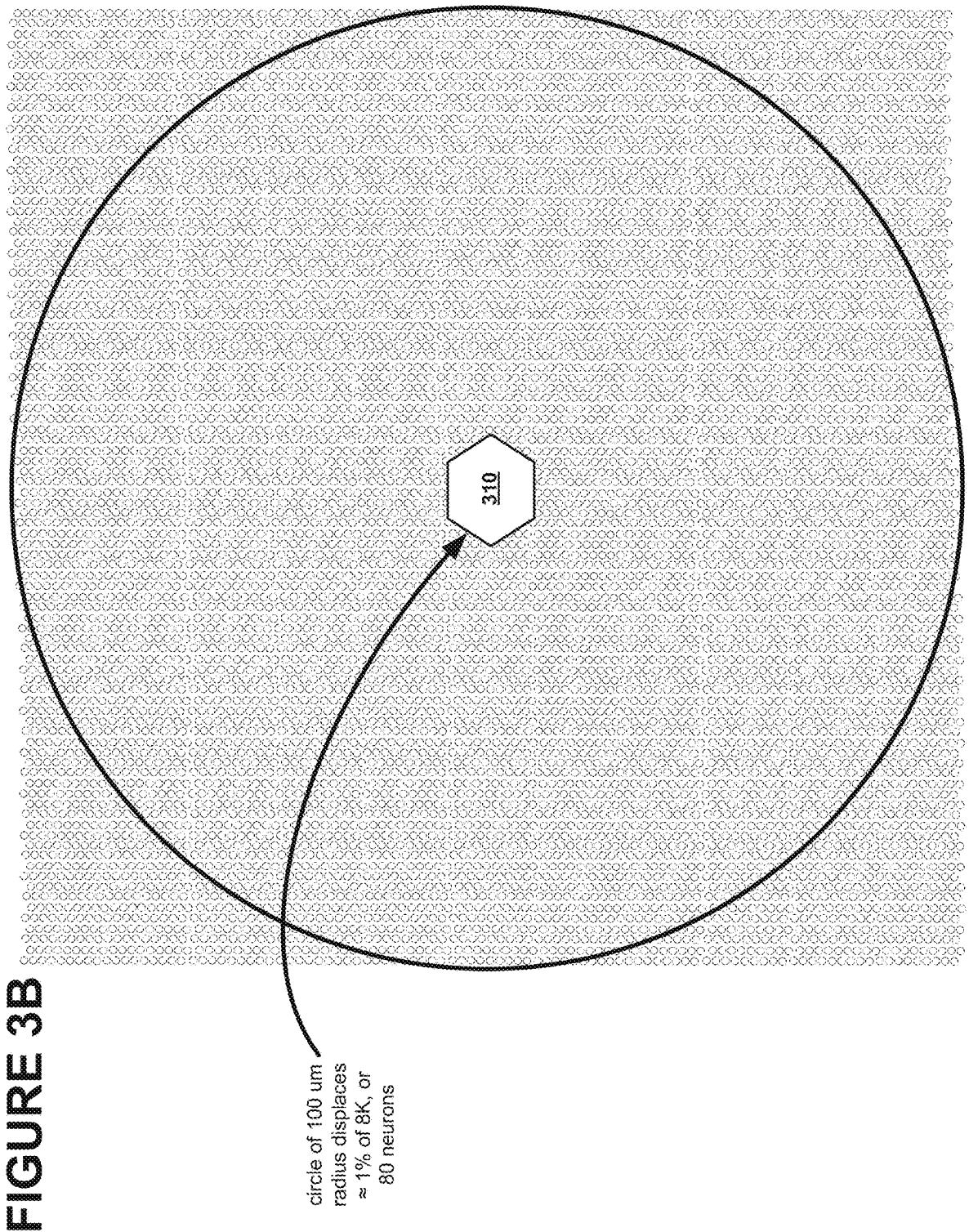
FIG. 3B presents same volume of cortical tissue as FIG. 3A, except shown from a top view.

FIG. 3B depicts the same top view of the cortical volume, as is shown in FIG. 2B, except that antenna 310 is shown as having been inserted. FIG. 3B also indicates that, per volume calculations, a 200 μm diameter antenna displaces about 1%, of the cortical neurons in that volume (80 neurons of 8000, for each of the approximately 37 neuronal layers, along depth 202). In general, this level of displacement can be expected to cause, at most, insignificant impairment to the normal functioning of the cortical matter into which it is inserted.

To (once again) suggest the density of neurons, across the cortical volume, cubic regions 312 and 313 are shown in FIG. 3A. These regions correspond to, respectively, 212 and 213 of FIG. 2A.

Figure 3C:
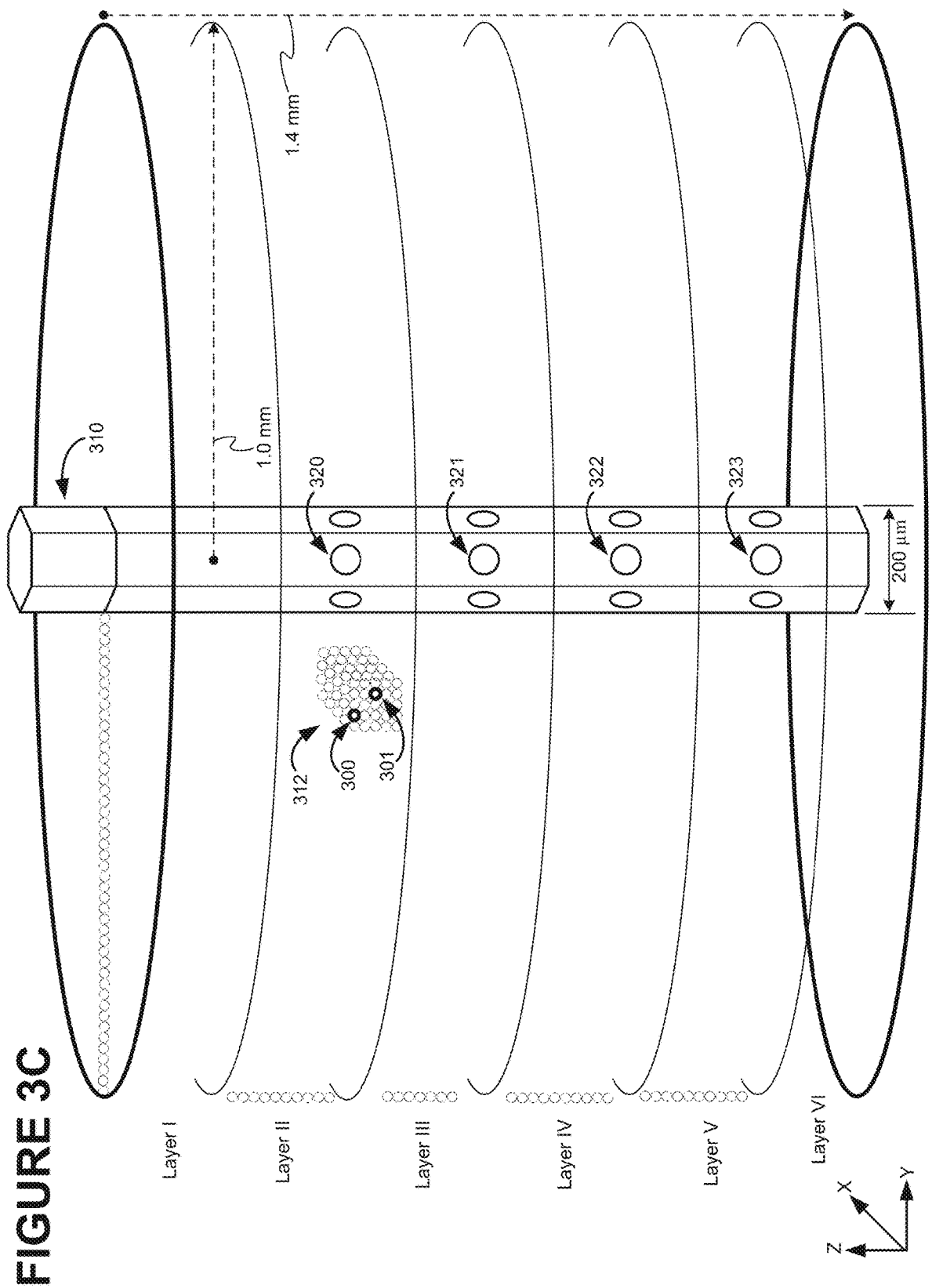
FIG. 3C is the same as FIG. 3A, except it focuses on two neurons, numbered 300 and 301, within cubic region 312.
Figure 3D:
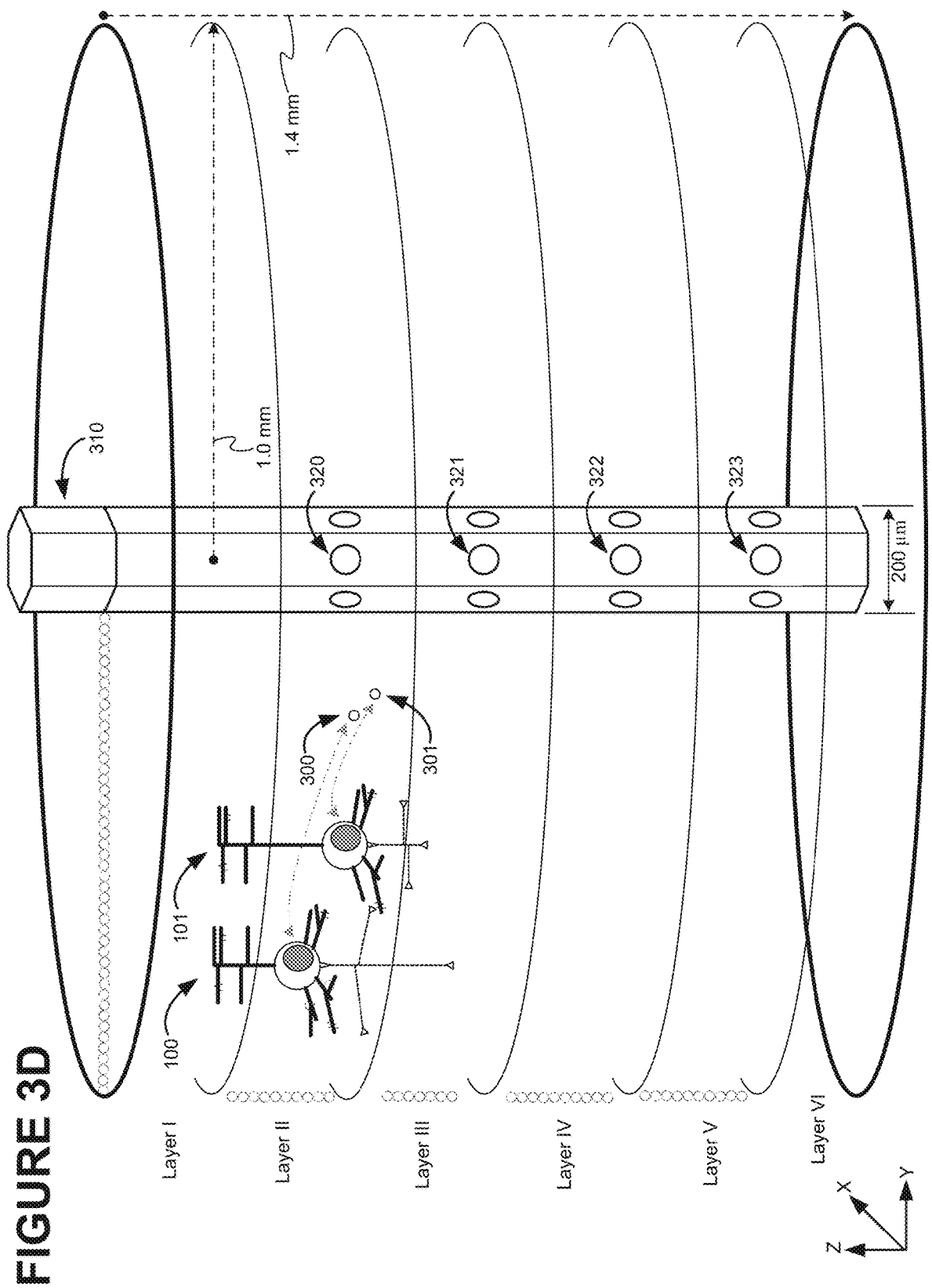
FIG. 3D relates neurons 300 and 301, of FIG. 3C, to, respectively, the connectivity between neurons 100 and 101, as discussed earlier with respect to FIG. 1B.

To provide some suggestion of inter-neuron connectivity, FIG. 3C focuses on two neurons, numbered 300 and 301, within cubic region 312. In FIG. 3D, each of neurons 300 and 301 is related to, respectively, the connectivity between neurons 100 and 101, as discussed earlier with respect to FIG. 1B. Thus, an axon collateral of neuron 100 is shown as connecting, laterally and within Layer II, to a dendritic branch of neuron 101. The apical dendrites, of both neuron 100 and neuron 101, are shown as extending upwards, into Layer I, before branching laterally to make connections with other neurons. Also, the main axon of neuron 100 is shown extending lower, down into Layer III. Of course, these few connections, provide only the most minimal hint, of the incredible richness of interconnectivity characteristic of mammalian cortical matter.

6 Injection Process

With regard to cortical tissue, IMD's can be applied to neurons through an injection process. FIG. 4A depicts a section of cortical tissue identical to that of FIG. 3A, except that, rather than an antenna structure 310, an injection needle 410 is shown as having been inserted. Compared to antenna 310, injection needle 410 is shown as being inserted only approximately halfway, into the depth of the cortical tissue (for the example cortical depth of 1.4 mm, injection depth 411 is shown as being approximately 0.7 mm). Injection needle 410 can be, for example, a 33 gauge blunt-ended needle (which has an outer diameter of approximately 200 μm).

FIG. 4B shows injection needle 410 coupled to a suitable syringe structure 412 that is supplied with any suitable injection fluid. For example, a phosphate buffered saline (PBS) solution can be used as the injection fluid. In this PBS solution can be suspended the IMD's.

Compared to FIG. 4A, FIG. 4B also shows additional types of tissue, for purposes of providing further context to the injection process. In particular, FIG. 4B shows additional tissue for a mammalian organism (e.g., a laboratory rat) into which the IMD's are to be introduced:
 A layer 432 of skull is indicated, through which a burr hole is shown as having been already drilled.
 Also indicated in FIG. 4B is dura mater layer 431, and cortical surface 430.

For both FIGS. 4A and 4B, an injection process is depicted that is just in its beginning stages. While at least hundreds of IMD's would be suspended in the PBS solution, as part of a typical injection process, for simplicity of exposition, FIG. 4B depicts only 7 IMD's, numbered 420-426. IMD's 424-426 are shown as still being in syringe section 412, while IMD's 421-423 are inside injection needle 410. Only IMD 420 is shown as having exited injection needle 410, along a trajectory labeled 412 (see FIG. 4A). Also, in FIG. 4A, IMD 420 is also shown as being in proximity to neurons located at cubic region 413. Actual entry of an IMD, into the soma of a neuron, is addressed in a following section that covers the inducement of endocytosis.

A sufficient concentration of IMD's can be suspended, such that only a small amount of the PBS solution (e.g., 0.5 microliters) need be injected at each cortical area where IMD's are to be introduced. Further, it is generally advantageous to apply the injection fluid slowly, at each injection site (e.g., over a two minute period). Concentration of IMD's, to a volume of injection fluid suitable to the particular application, can be achieved, for example, by use of a centrifuge.

Because of their small size, the IMD's can be expected to distribute themselves throughout the tissue area that is in proximity to each injection site, in a manner similar to that achieved when particular molecular compounds are injected into various kinds of tissue. The fluid dynamics, of the PBS solution as it comes into contact with the cortical tissue, can be expected to exhibit various flow patterns, which aid in an even distribution, among the cells of the cortical tissue to be studied. Further, the IMD's themselves are sufficiently small, such that they can be expected to undergo secondary effects, such as Brownian motion, that also encourage a more uniform distribution, of IMD's within the cortical cells.

Figure 4C:
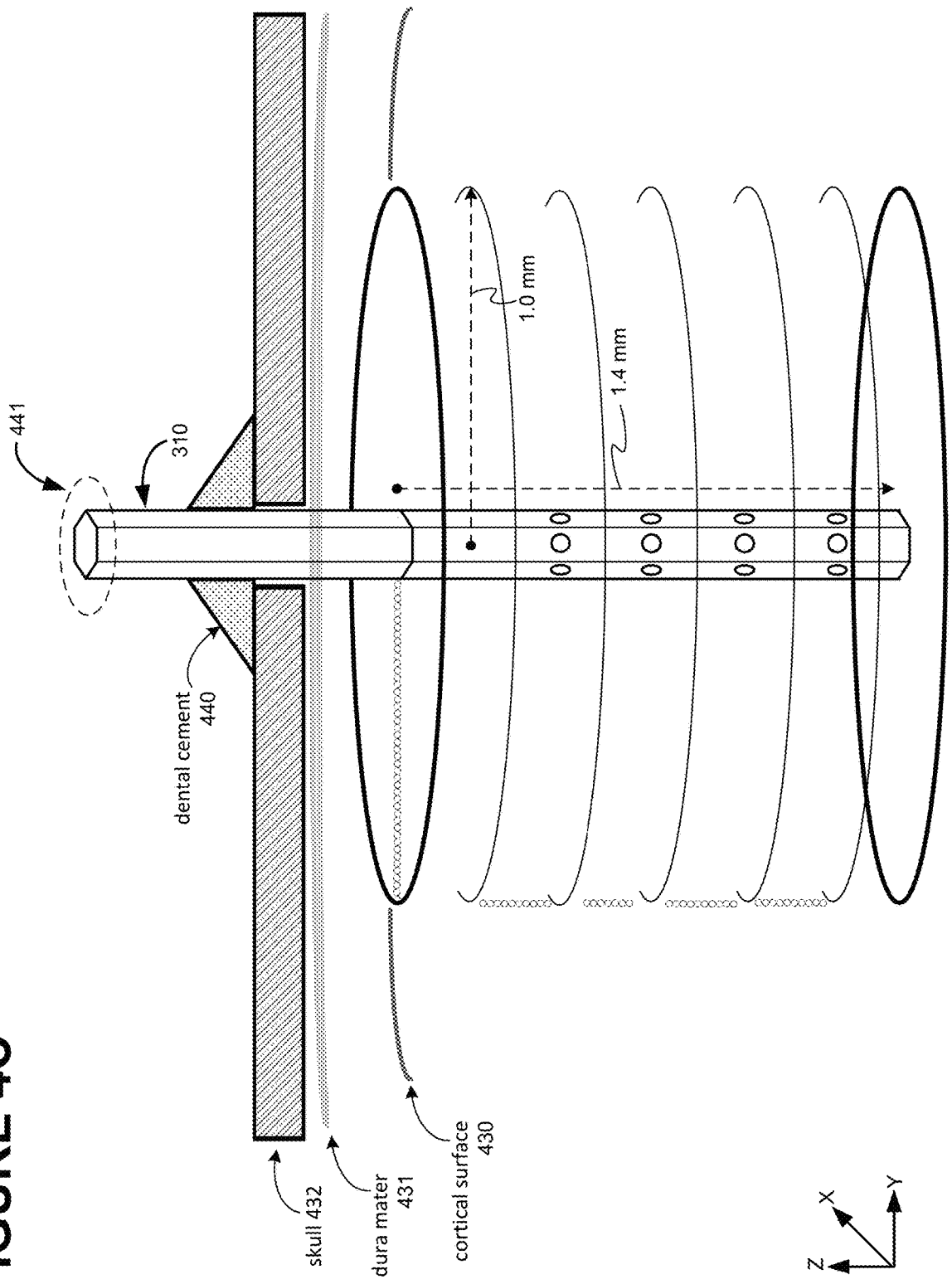
FIG. 4C is similar to FIG. 3A, but shows how antenna 310 can be secured in-place, with respect to skull surface 432.

Once injection of the IMD's has been accomplished, injection needle 410 can be removed, and, as is shown in FIG. 4C, replaced with an antenna 310. The drawing of FIG. 4C is the same as FIG. 3A, except the broader context, of mammalian bodily tissue, is shown. As can be seen, antenna 310 can be secured in-place, with respect to skull surface 432, by the application of dental cement 440.

7 EM Collection

Once IMD's have been placed inside the cells to be monitored, and an antenna is in-place with respect to the tissue to be monitored, the antenna can be used to collect EM transmissions from the IMD's.

As discussed previously, the particular example structure, of antenna 310, has four EM collection points per side. Further, antenna 310 has a hexagonal structure, meaning there are a total of 24 EM collection points. With respect to IMD's transmitting in the NIR part of the spectrum, each collection point can be implemented with a collimating lens, referred to herein as a nano-collimating lens (or NCL). Each NCL can be coupled to an optical fiber, such that the NIR signals received can be transported to appropriate receiving equipment.

Figure 4E:
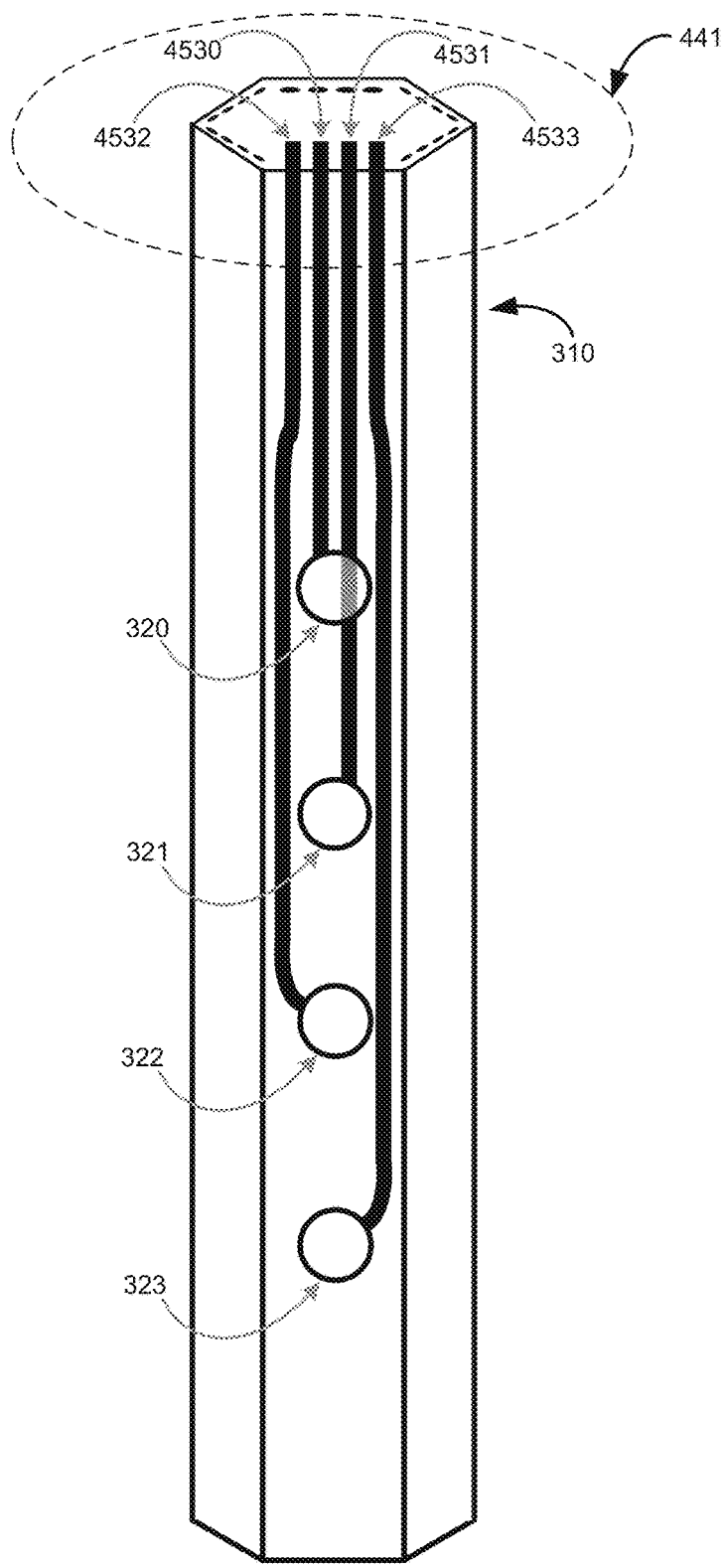
FIG. 4E shows each EM collection point being implemented with a nano-collimating lens, and each such lens being coupled to an optical fiber.

An example of this approach is shown in FIG. 4E, where EM collection points 320-323 are shown as each being implemented with an NCL and each of the NCL's is coupled to, respectively, one of optical fibers 4530-4533. FIG. 4D shows that, following this approach, 24 optical fibers emerge from top-surface 441 of antenna 310. Four optical fibers are shown emerging from each of the six sides of antenna 310, the sides numbered (clockwise) 450-455. For an antenna 310 with a diameter of 200 µm, it can be seen that each side of the antenna is 100 µm wide, meaning that each NCL needs to have a diameter less than 100 µm.

The 24 optical fibers, coupling antenna 310 to the receiving equipment, can be of a length suitable for the particular experimental situation. For example, if the optical fibers couple a laboratory rat to the receiving equipment, and the ensembles of rat cognition are to be studied (e.g., see above discussion of the Cruz et al. paper), it is necessary the optical fibers are of sufficient length, such that the rat can have sufficient mobility, when interacting with an environment in which it is placed. Optical fibers, without any further structural support, are fragile. Any suitable cabling technique can be used, to wrap the 24 fibers in a suitably strong protective covering.

Figure 10:
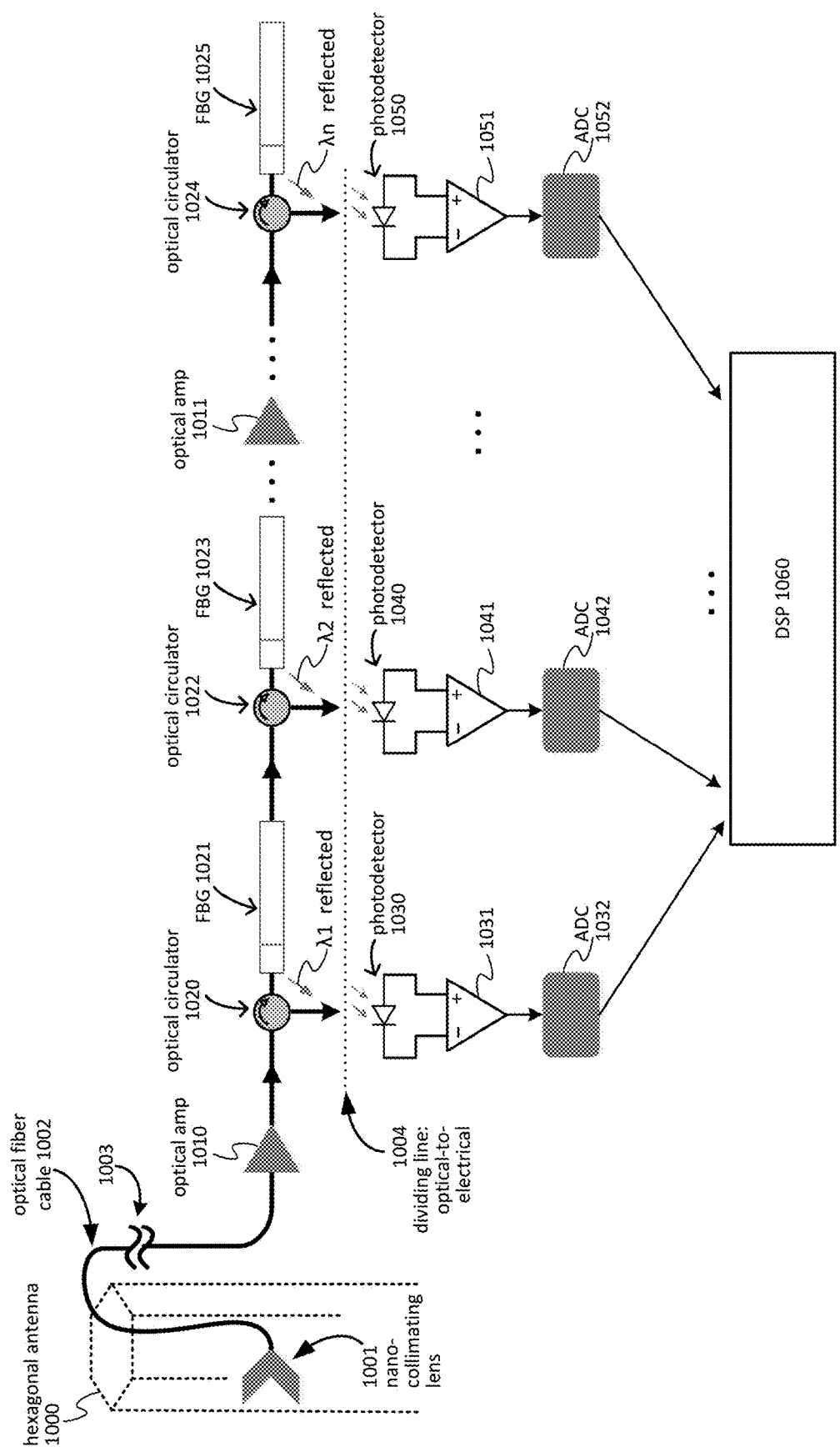
FIG. 10 depicts an example signal processing, in the optical and electrical domains, for each nano-collimating lens of antenna 310.

FIG. 10 depicts an example coupling, between a single NCL and its receiving equipment. In FIG. 10, antenna 310 is represented by dotted outline 1000. Within this outline, only a single NCL 1001 is shown (although a total of 24 NCL's would be needed). The NIR collected by 1001 is directed along an optical fiber 1002. Fiber 1002 is sized to be of sufficient length, such that it provides suitable mobility for a test animal (the variable length of 1002 represented by break 1003).

The "NCL Receiving Equipment," as that term is used herein, consists of all the equipment in FIG. 10 that is coupled to the output of fiber 1002. The NCL Receiving Equipment begins with optical amplifier 1010, which is driven directly by the output of fiber 1002. Optical amplifier 1010 then drives, directly or indirectly, all the other NCL Receiving Equipment for NCL 1001. Optical amplifier 1010 is the first component of the NCL Receiving Equipment because the NIR signal, expected to be provided at the output of fiber 1002, is otherwise too attenuated for frequency analysis. Any suitable optical amplification technology can be used, so long as it includes at least the following characteristics:

- only increases the amplitude, of the NIR collected by its NCL;
- does not remove or add any frequency components; and
- relative amplitudes, between frequency components, is unchanged.

Only a single copy of the NCL Receiving Equipment of FIG. 10 is shown, since it is only necessary to provide a copy, of the same apparatus, for each of the 23 other NCL's.

The output of optical amplifier 1010 is subjected to, in the optical domain, a frequency analysis. As was discussed above, a technique for identifying the IMD, that is the source of a particular signal, is to assign each IMD a unique frequency, where all such frequencies chosen are within the NIR band of EM radiation. Thus, a task of the NCL Receiving Equipment can be to determine which frequencies, of the frequencies assigned to IMD's, are present in the collected signal. This task can be accomplished by equipping the NCL Receiving Equipment with either a set of optical notch filters (one for each of the possible IMD frequencies), or by using an optical spectrum analyzer, such as a spectrum analyzer based upon a diffraction grating. FIG. 10 presents the approach of using a set of optical notch filters.

Specifically, FIG. 10 presents the use of Fiber-Bragg Gratings (FBG's), where each FBG is tuned to a wavelength to be detected. While only three FBG's are explicitly shown in the FIG. 10 (numbered 1021, 1023, and 1025), FIG. 10 makes it clear that, in general, the apparatus can contain "n" FBG's:

- FBG 1021 is tuned for a wavelength $\lambda 1$;
- FBG 1023 is tuned for a wavelength $\lambda 2$; and
- FBG 1025 is tuned for a wavelength $\lambda n$.

Based on the NCL Receiving Equipment architecture of FIG. 10, "n" is expected to be in the following range:

$$(\text{approximately } 100) \leq n \leq (\text{approximately } 1000)$$

Using the approach of assigning a unique frequency to each IMD, this means injecting 100 to 1000 IMD's within each separately-monitored region of cortical tissue.

An FBG works as a kind of specialized optical fiber. Light input to it, which is not of the frequency for which it is tuned, simply passes straight through. However, if the input light has a component that is at the FBG's frequency, that component is reflected backwards, towards the input to the FBG. This filtering property, of an FBG, can be utilized by combining the FBG with another kind of optical device, called an "optical circulator." For the NCL Receiving Equipment of FIG. 10, for example, optical circulator 1020 is the only component directly connected to the output of optical amplifier 1010.

Before describing how an optical circulator can be used with an FBG, it is useful to describe how it operates on its own. As shown in FIG. 10, each optical circulator has three connection points or ports: a left-side port, a right-side port, and a bottom port. All light entering the left-side port simply passes straight through, and exits at the right side port of the optical circulator. Any light entering the right-side port, however, does not pass straight through, and does not exit at the optical circulator's left side port. Rather, such light is direct downwards, and exits from the bottom port of the optical circulator.

The combination of optical circulator 1020 and FBG 1021 works as follows. First, all light entering the left port of optical circulator 1020 simply passes through, and exits the right port. The light exiting the right port then enters FBG 1021. If the light entering FBG 1021 contains no λ1 component, all the light simply passes straight through, and enters the next stage of filtering (comprised of optical circulator 1022 and FBG 1023).

To the extent the light entering FBG 1021 contains a λ1 component, the path of this component is as follows. It is reflected backwards, and into the right port of optical circulator 1020. The λ1 NIR then exits the bottom port of optical circulator 1020. This emerging NIR of λ1 is detected by a photodetector 1030. Photodetector 1030 is shown as a photodiode, but any suitable photodetecting technology can be used. For example, CCD-based photodetectors are suitable. The current produced by photodetector 1030 is then amplified, so that it can be sampled, with the samples digitized by an Analog-to-Digital Converter (or ADC) 1032. The output of photodetector 1030 is shown as being amplified by a differential amplifier 1031, but any suitable amplifier can be used. As can be seen, the lower port of optical circulator 1020 is separated from photodetector 1030 by a dashed line 1004. Dashed line 1004 is meant to clarify the transition, within the NCL Receiving Equipment, from the optical domain of signal processing to the electrical domain.

The net effect, of optical circulator 1020 and FBG 1021, is that they act as an optical notch filter, directing any λ1 component though the circulator's bottom port, and directing any non-λ1 NIR to the next optical notch filter.

In the case of FIG. 10, the next optical notch filter is formed from optical circulator 1022 and FBG 1023. This second notch filter works the same as the first, except it filters for a λ2, rather than λ1. Just as with the λ1 filter, any λ2 component, to the light that enters the left port of optical circulator 1022, is reflected backwards, by FBG 1023, and into the right port of optical circulator 1022. This λ2 NIR exits the bottom port, where it can then be detected by photodetector 1040. The transition from optical to electrical domain is once again emphasized by dashed line 1004, which is in-between optical circulator 1022 and photodetector 1040. The photodetector's output is once again amplified (this time by 1041), sampled, and digitized (this time by ADC 1042).

As discussed above, this type of linear chaining, of optical notch filters, can be extended to the point where it includes filters for hundreds of specific wavelengths. To achieve filter chains of 100, or more, filters in length, there is a periodic need for additional optical amplifiers, such that the passed-through NIR can be boosted back to a sufficient amplitude for further frequency analysis. The periodic inclusion of one or more additional optical amplifiers is represented, in FIG. 10, by optical amplifier 1011. It is necessary that each additional optical amplifier share the same three characteristics, listed above, for optical amplifier 1010.

The outputs of all the various filter stages, for the NCL Receiving Equipment of FIG. 10, are shown feeding into a common Digital Signal Processing (DSP) block 1060. DSP 1060 can be used to identify all the pulses received, by NCL 1001, that correspond to a strongly activated neuron. For all "n" wavelengths monitored by the NCL Receiving Equipment, DSP 1060 can output a data stream representing the pulses detected. The ADC's, whose outputs feed into DSP 1060, need to sample at a sufficiently high rate, such that the strong-activation neural pulses can be detected. As discussed above, a typical pulse width is 10 ms. However, to provide support for a broader range of neural pulses, the ADC's can be designed, for example, for neural pulse widths as small as 1 ms. To satisfy the minimum Nyquist sampling rate, this corresponds to each ADC sampling at 2 kHz. To provide extra resolution, beyond this minimum, each ADC can sample at, for example, 10 kHz.

In order to be able to compare the amplitudes of pulses detected at each particular A, across the outputs of all 24 DSP blocks (because there is one DSP block for each copy of NCL Receiving Equipment), it can be useful to match characteristics, across all 24 optical amplifiers occupying a same location in the chain of notch filters. The outputs of the 24 DSP blocks can then be combined, using any suitable pulse-matching techniques, to produce a single reconstructed stream of strong-activation neural pulses. For example, the following types of pulse-matching techniques can be used:

Detecting an IMD pulse from multiple NCL's, at the same time, can increase confidence in a conclusion that a true IMD pulse had been detected.

Among the NCL's that receive a same-frequency IMD pulse at a same time, the amplitude of the pulse can be set as equal to the strongest amplitude detected.

A structured searched can be performed, of the 24 data streams, in order to obtain some location information on the source of an IMD pulse. For example, for a hexagonal antenna, since any three consecutive sides represent 180°, an IMD pulse can be received by, at most, three sides. For any one IMD pulse, the sides that detected it can be found by searching through all six possible combinations of three consecutive sides. For each of these six possibilities, the following can be performed:

For each pulse detected by one or more NCL's of the middle side, it can be pattern-matched against the pulses found by its two adjacent sides.

If the middle side detects a pulse with the greatest amplitude, compared to the greatest amplitude detected for the same pulse at the other two sides, we can conclude that the IMD, that generated the pulse received by the middle side, must be most directionally aligned with that middle side.

On the other hand, if a pulse detected by the middle side has a greater amplitude at one of the adjacent sides, analysis of that pulse can be deferred, until that adjacent side is considered as the central side.

8 IMD, Example Construction

8.1 Overview

An example specific structure for an IMD, along with techniques for its manufacture, is covered in this section.

Figure 5A:
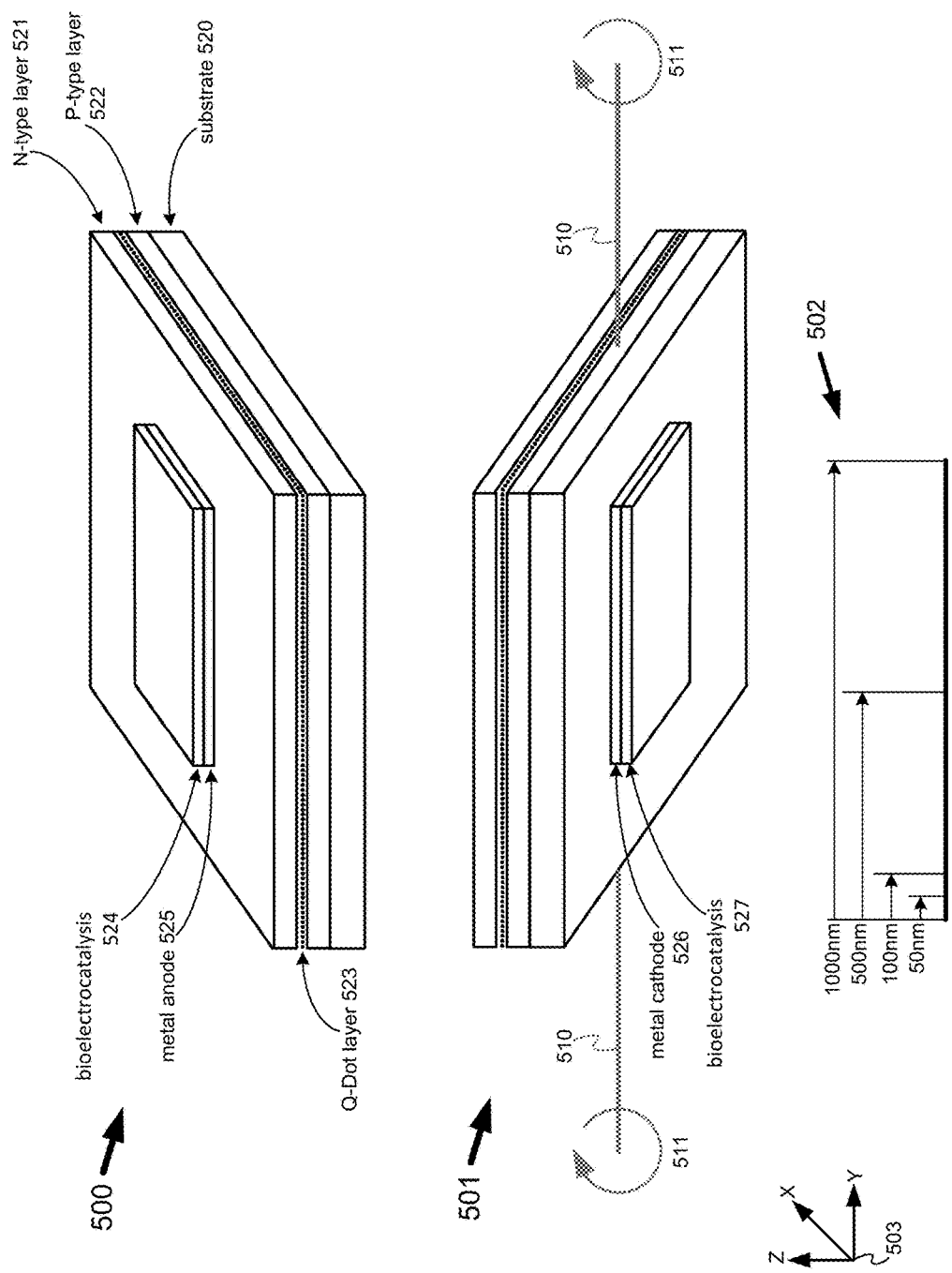
FIG. 5A presents two perspective views, 500 and 501, of a same example IMD design.

FIG. 5A presents two perspective views, 500 and 501, of a same example IMD design. The main body of the IMD is shown, in view 500, as being constructed from a substrate 520, that has its major dimensions in the X-Y plane (as indicated by set of axes 503).

On this substrate have been manufactured the following layers, starting from the layer that is directly in contact with the substrate and proceeding upwards (these layers have the same dimensions, along the X-Y plane, as 520):

P-type layer 522;
Quantum dot (or QD) layer 523; and
N-type layer 521.

In the X-Y plane, example dimensions for layers 520-523 is 1000 nm (or 1 μm) per side, forming the shape of a square. This dimensionality can be seen from scale 502 (see bottom of FIG. 5A). Also, FIG. 5B shows the same two views as are depicted in FIG. 5A: views 500 and 501 of FIG. 5A are the same as, respectively, views 504 and 505 of FIG. 5B. In view 504, the dimensionality of layers 520-523, along the X-Y plane, are indicated as distance 540 (along the X axis) and distance 541 (along the Y axis). Further, view 504 highlights a corner of this four-layer structure, indicated by dashed outline 530. The corner is depicted, in magnified form, in FIG. 6.

Figure 6:
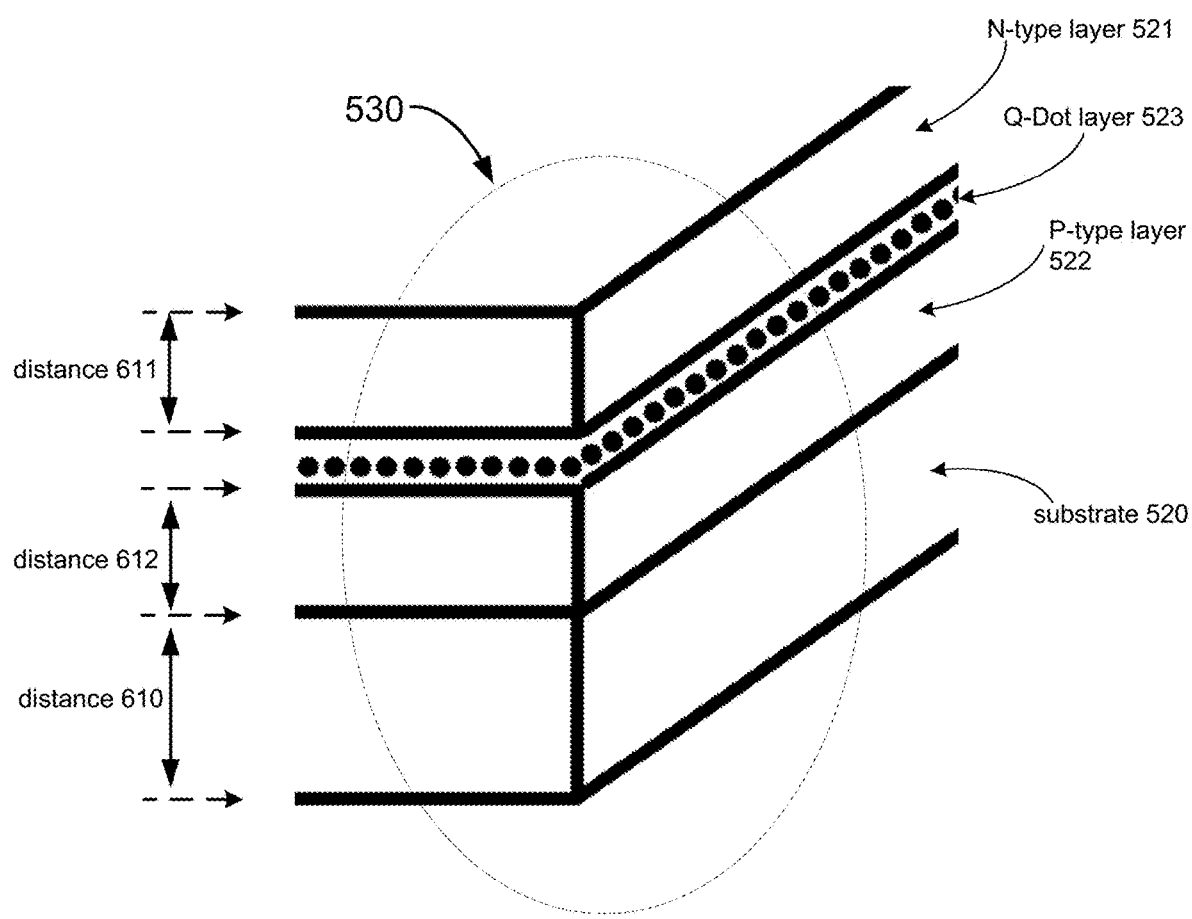
FIG. 6 shows a highly magnified view of region 530, as indicated in FIG. 5B, and labels the thicknesses.

FIG. 6 shows the thickness (i.e., the distance along the Z dimension), of each of layers 520-522, as, respectively, distances 610-612. From scale 502, at the bottom of FIG. 5A, each of layers 520-522 can be estimated as having, respectively, the following approximate thickness: distance 610 is 75 nm, distance 611 is 50 nm, and distance 612 is 50 nm. An example range of thicknesses, for quantum dot (or QD) layer 523, is about 2 nm to 10 nm. Adding together the thicknesses, of layers 520-523, results is a net thickness (indicated as distance 542 in view 504 of FIG. 5B) of about 177 nm to 185 nm (depending upon the thickness of quantum dot layer 523).

8.2 Quantum Dot LED

Figure 5C:
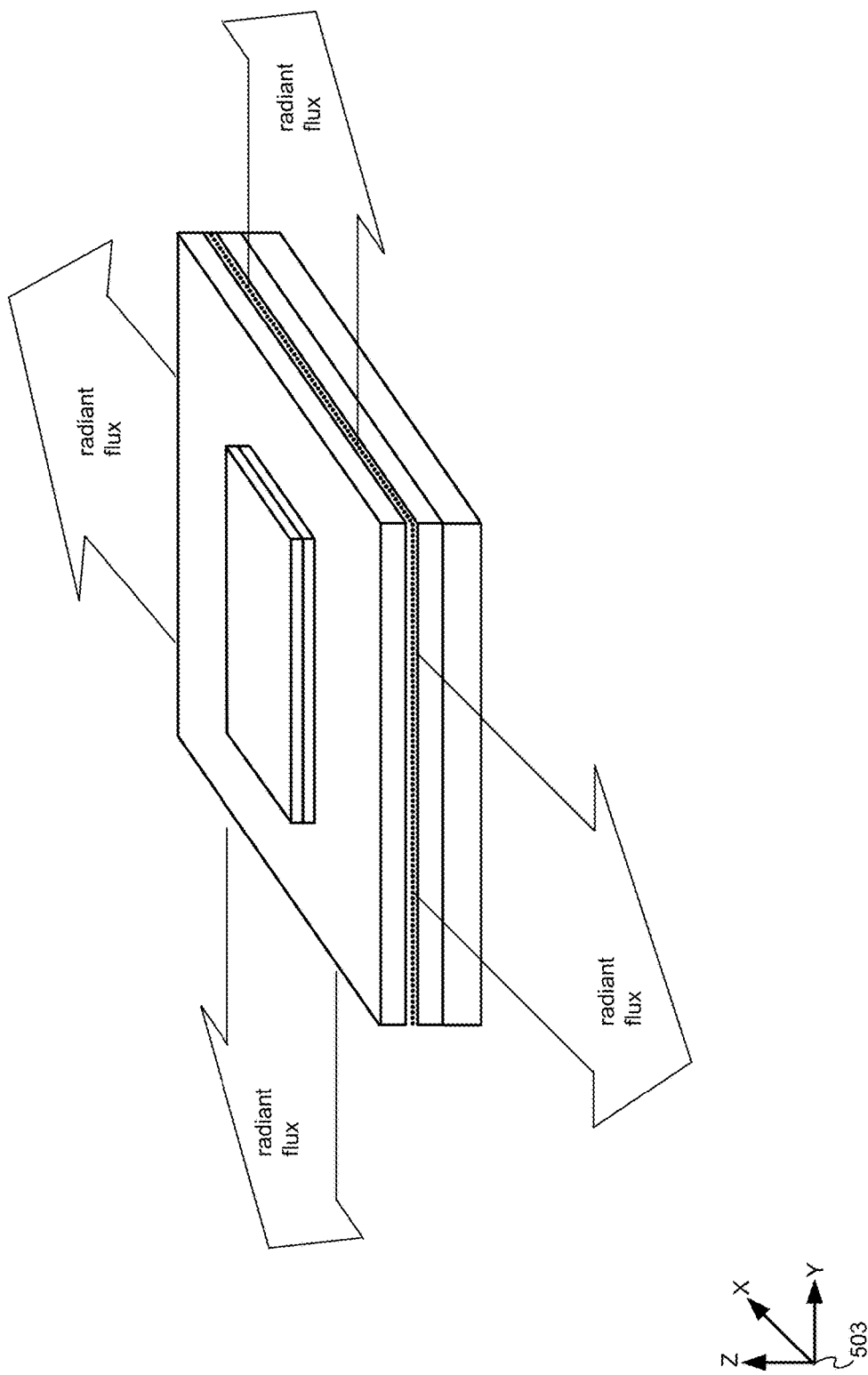
FIG. 5C depicts NIR as it would radiate, in the X-Y plane, for the IMD design of FIGS. 5A-B.

Layers 521-523 form the core of a Quantum Dot Light-Emitting Device (also called a QD-LED). Quantum dot layer 523 emits light when the voltage, between P-type layer 522 and N-type layer 521, is at or above a threshold voltage (that we shall refer to as $V_{TH}$). For the row of quantum dots, on each of the four 1 μm sides of the IMD, an example path for the radiant flux (e.g., NIR) produced, when at least $V_{TH}$ is applied, is shown in FIG. 5C. FIG. 5C depicts NIR as radiating only in the X-Y plane, for simplicity of illustration. In general, however, NIR can be expected to radiate, from each 1 μm side, at angles projecting both above and below the X-Y plane.

A wide range of QD-LED designs are known, and a suitable QD-LED design can be chosen, depending upon the particular application. For example, QD-LED design is discussed in the following publications, each of which is herein incorporated by reference in its entirety:

"Tuning the performance of hybrid organic/inorganic quantum dot light-emitting devices," by Coe-Sullivan et al., in Organic Electronics, Volume 4, September 2003, pages 123-130 ("the Coe et al. paper"); and "Contact Printing of Quantum Dot Light-Emitting Devices," by Kim et al., in Nano Letters, Volume 8, No. 12, Nov. 2008, pages 4513-4517 ("the Kim et al. paper").

In such designs, based on the Organic Light-Emitting Diode (OLED), the N-type and P-type layers are often referred to as, respectively, the Electron Transport Layer (ETL) and the Hole Transport Layer (HTL). As the name implies, both layers are constructed from organic materials. For example, the Coe et al. paper and the Kim et al. paper describe the following:

an organic compound known by the acronym "TPD" as an example HTL material;

an organic compound known by the acronym "Alq$_3$" as an example ETL material; and CdSe as an example compound for the QD's.

QD's can be formed from a variety of different compounds, besides CdSe. Alternative compounds are discussed in such publications as the following, herein incorporated by reference in its entirety:

"Size-dependent band gap of colloidal quantum dots," by Baskoutas et al., in Journal of Applied Physics, Volume 99, Issue 1, January 2006, 4 pages ("the Baskoutas et al. paper").

In addition to CdSe, the Baskoutas et al. paper discusses the following, as materials from which QD's can be formed: CdS, CdTe, PbSe, InP, and InAs. InAs can be a particularly good material from which to make QD's, because it can result in QD-LED's that require a lower threshold voltage (or $V_{TH}$). For the specific embodiment of the invention discussed herein, where power is provided by a process called bioelectrocatalysis (as described below in Section 8.4), this property can be useful.

The overall principle of operation of a QD-LED, when a sufficient threshold voltage is applied, is as follows. The applied electric field causes electrons from the ETL (e.g., layer 521) and holes from the HTL (e.g., layer 522) to move toward the QD layer (e.g., layer 523), that is between the ETL and HTL layers. The electrons and holes are both captured by the quantum dots, where they recombine, resulting in the emission of photons.

As between HTL and ETL materials, it is generally the case that organic HTL materials transport holes more effectively than ETL materials transport electrons. If not compensated for, this leads to an undesirable tendency for electrons and holes to combine closer to the source of the electrons, than to the source of the holes, reducing the number of electron-hole recombinations that could otherwise occur in the QD layer. This problem tends to be addressed by adding a hole-blocking layer, at an appropriate location in-between the ETL and HTL. An example hole-blocking material, discussed in the Coe et al. paper and the Kim et al. paper, is an organic compound known by the acronym "TAZ." This type of hole-blocking layer is not shown in either of FIG. 5A or 5B. Other potential refinements for a QD-LED are also not shown in the figures, as they are not relevant to the present invention, but can be added, as needed, for particular applications.

8.3 Substrate and Metal Layers

An example semiconductor manufacturing process by which a suitable substrate, for the three above-described layers (layers 521-523), can be constructed, is called Silicon on Sapphire (or "SOS"). The present invention utilizes semiconductor fabrication technology in a way that is counter to one of the industry's major trends: the trend towards larger die sizes. SOS is a particularly good process for the present invention because of the very small die size (e.g., 1 μm by 1 μm) needed for an IMD. These dimensions are much smaller than what is typically required, from an integrated circuit fabrication process. Prior to the present invention, die have almost always had a per-side length in the range of $1.0 \times 10^{-3}$ m to $2.0 \times 10^{-2}$ m. Thus, the IMD die size of $1.0 \times 10^{-6}$ m is at least three orders of magnitude smaller than the low-end of conventional die sizes.

Typically produced by use of a diamond saw, die are cut from a much larger wafer (e.g., common semiconductor processes handle wafers with a diameter in the range of about 70 mm to 300 mm). In general, in a non-SOS process, when the wafer is cut to create die that are of a size required by the present invention, the likelihood is much greater for substrate cracking. However, SOS is only an example, and any other fabrication process, so long as it has similar resistance to cracking (and sufficiently small feature sizes), can be used.

The other major industry trend, towards smaller feature sizes, is useful towards the construction of more sophisticated IMD's, but die size itself is limited, due to the size of a biological living cell.

On top of N-layer 521 are shown two additional layers (starting from the layer that is directly in contact with 521 and proceeding upwards):

Metal layer 525, shown as being about 25 nm along the Z dimension.

Bioelectrocatalysis layer 524, the thickness of this layer depending upon the particular enzyme used.

As with layers 520-523, layers 524-525 also have their principal dimensions in the X-Y plane, but, within that plane, layers 524-525 occupy less area (e.g., pictured in FIG. 5A as occupying about ¼ to ⅓ the area of layers 520-523, and generally centered within that area).

View 501 of FIG. 5A shows the same IMD of view 500, but the IMD has been rotated. View 501 depicts an axis 510, about which the IMD of view 500 has been rotated, in the direction indicated by 511. This rotation permits the "underside" of the IMD to be seen in view 501. The underside of the IMD is very similar to its top. Below substrate 520 are shown two additional layers (starting from the layer that is directly in contact with 520 and proceeding downwards):

Metal layer 526, shown as being about 25 nm along Z dimension.

Bioelectrocatalysis layer 527, the thickness of this layer depending upon the particular enzyme used.

As with layers 524-525, layers 526-527 also have their principal dimensions in the X-Y plane, and, within that plane, occupy less area than layers 520-523 (e.g., pictured in FIG. 5A as occupying about ¼ to ⅓ the area of layers 520-523, and generally centered within that area). However, other than a need to provide sufficient room for inducement of endocytosis (see below section entitled "Endocytosis"), it is generally desirable that layers 524-525 and 526-527 occupy an area as close as possible to that of layers 520-523, since greater area for the bioelectrocatalysis layers means greater electric power production, for purposes of driving an IMD's QD-LED.

The purpose of metal layers 525 and 526 is to provide electrical contact with, respectively, N-type layer 521 and P-type layer 522. Since metal layer 526 is separated from the P-type layer by substrate 520, contact between layers 526 and 522 can be accomplished by utilizing Through-Substrate Vias (or TSV's), as is well-known in the semiconductor fabrication industry. Other than the need for TSV's, metal layers 525 and 526 are, in themselves, a common part of QD-LED construction, as described in many publications on this topic, just a sample of which have been discussed above: the Coe et al. paper, the Kim et al. paper, and the Baskoutas et al. paper.

Adding bioelectrocatalysis layers 524 and 527, however, in order to provide a power source for a QD-LED, is one of many inventive techniques presented herein. The operation of the bioelectrocatalysis layers, as a power source for an IMD, is presented in the following section.

As addressed in an earlier section, an alternative or additional power source for each IMD can be obtained through broadcast power. In this case, metal layers 525 and 526 can be used as a kind of dipole antenna. The tissue into which the IMD's have been injected can be exposed to EM radiation of a suitable frequency, such that sufficient electrical energy is produced from the dipole antenna (formed from layers 525 and 526). For example, a horn antenna can be used to expose the tissue to broadcast power of sufficient amplitude. While dipole antennas are typically discussed as a half-wave design, the dipole of an IMD can represent a smaller (perhaps much smaller) fraction of the wavelength of the broadcast power. Capturing a smaller fraction of the wavelength merely reduces the efficiency of the antenna, but the power produced for an IMD can still be sufficient.

8.4 Bioelectrocatalysis 8.4.1 Overview

Assuming bioelectrocatalysis has been selected as the power source (or a power source) of the IMD's to be monitored, this section presents an example, specific, embodiment for doing so. While the enzyme presented herein (i.e., NADPH reductase) has been selected to monitor neural activity, it can readily be appreciated that other kinds of enzymes can be substituted, such that other kinds of intracellular activity can be monitored. For example, with a different enzyme, the bioelectric catalysis, to power the herein-described IMD, can be switched on when a certain glucose level is reached.

With regard to monitoring neural activity, however, NADPH reductase (produced from NO synthase) can be used as the enzyme of which layer 524 is constructed. NADPH reductase is selected because it is activated, as an enzyme, only when the neuron in which it is contained is strongly activated (the connection, between neuron activation and enzyme activation, is explained below). When activated, the NADPH reductase produces an electric current at about −0.4 volts (i.e., it is a source of electrons). This −0.4 volts is available at metal layer 525 (which is why this metal layer is called an anode).

Laccase can be used as the enzyme, of which layer 527 is principally constructed. When provided with a source of electrons (i.e., the electrons provided by the above-described NADPH reductase), the laccase produces an electric current at about +0.8 volts. This +0.8 volts is available at metal layer 526 (which is why this metal layer is called a cathode).

When a neuron is strongly activated, the net voltage between the cathode 526 and anode 525 can be expected to be about +1.2 (i.e., +0.8−−0.4=+1.2). When a neuron is not strongly activated, a relatively negligible net voltage can be expected to occur, between cathode 526 and anode 525. An example of a separation level, between voltages that are negligible and those that are not, is the following value: a voltage that is approximately one order of magnitude smaller, than the net voltage produced when a neuron is strongly activated. Any voltage that is equal to or less than this separation level can be regarded as negligible.

The QD-LED, formed by layers 521-523 and 525-526, is designed, by suitable selection of materials, to require a $V_{TH}$ that meets both of the following constraints:

$V_{TH}$ is higher than the voltage produced when the neuron is not strongly activated (e.g., $+0.12 < V_{TH}$); and $V_{TH}$ is less than, or equal to, the voltage produced when the neuron is strongly activated (e.g., $V_{TH} \leq +1.2$).

The next result, of making $V_{TH}$ meet the above-two constraints, is that the IMD only emits NIR when the neuron, in which it is embedded, is strongly activated.

As discussed above, one technique, for changing the threshold $V_{TH}$ of a QD-LED, is to change the material from which the QD's are formed. A QD formed from CdSe can be expected to have a $V_{TH}$ of about +1.2 volts. Therefore, depending upon the application, the bioelectrocatalysis-supplied power may be regarded as too unreliable, for causing an IMD to emit NIR. For this reason, QD's can be formed from InAs, which provides a lower threshold voltage. In order to construct a QD-LED that produces a λ anywhere in the NIR range (approximately 700 nm to approximately 1100 nm), the diameter of its InAs QD's should be in the range of approximately 1.0 nm to approximately 3.0 nm. The smaller diameters produce higher frequencies, while the larger diameters produce lower frequencies. The size range for NIR-generating InAs QD's is based upon the model in the Baskoutas et al. paper.

The connection, between strong activation of a neuron and activation of the NADPH reductase, is as follows. NADPH reductase is activated when it is exposed to an aqueous solution that has a sufficient concentration of calcium ions (i.e., $Ca^{2+}$). Research has determined that increased activation of a neuron is reliably indicated by its soma achieving an increased concentration of calcium ions. Only when a neuron reaches strong activation, however, does its concentration of calcium ions become sufficient to activate NADPH reductase (with the neuron's cytoplasm acting as the aqueous solution to which the NADPH reductase is exposed).

8.4.2 Molecular Level

Although bioelectrocatalysis layers 524 and 527 are shown in FIG. 5A as each being very similar to its adjacent metal layers, respectively, 525 and 526, they are, in fact, quite different. Layer 524 is a type of coating, comprised mainly of enzyme molecules attached to metal layer 525. Each enzyme molecule is anchored to the metal layer with a simpler linker molecule. In addition to its anchoring function, each linker molecule also acts as a kind of "wire," that guides electrical energy, created in the relative interior of an enzyme molecule, out to the metal layer, where it can be used to power the IMD's QD-LED. Similarly, layer 527 is also a kind of coating, comprised primarily of enzyme molecules that are attached to metal layer 526. As with layer 524, each enzyme molecule of layer 527 is relatively large and complex. A simpler linker molecule is used to both anchor each enzyme molecule to layer 526, and to provide a kind of "wire," for guiding electrical energy from the relative interior of an enzyme molecule.

8.4.2.1 Anode

For the IMD design, as shown in view 504 of FIG. 5B, a corner region 531, of layers 524 and 525, is indicated. Region 531 is shown in magnified form in FIG. 7A. Like FIG. 5B, FIG. 7A continues to show layer 525 as a homogeneous metal layer (labeled "anode" in FIG. 7A). The increased magnification of FIG. 7A, however, permits layer 524 to be shown quite differently.

Layer 524 is composed primarily of relatively large and complex NADPH reductase molecules (the enzyme). Each NADPH reductase molecule, of FIG. 7A, is represented in greatly simplified form as a sphere, rather than as a ribbon diagram. For each NADPH reductase molecule, only its outer perimeter is indicated, in a first-order approximate way, by the spherical outline. As shown on the right side of FIG. 7A, region 531 encloses five NADPH reductase molecules, one of which is labeled 710. The left side of FIG. 7A focuses just upon NADPH reductase molecule 710.

While not specifically shown, each NADPH reductase molecule, comprising layer 524, also includes the small molecule cofactor Flavin Adenine Dinucleotide (FAD). As part of an IMD manufacturing process, the FAD is typically already added to the NADPH reductase, prior to the NADPH reductase molecules being attached to metal anode 525.

In addition to the NADPH reductase molecules, layer 524 is also shown as including linker molecules. For each NADPH reductase molecule, it is anchored to the anode by a corresponding linker molecule. For example NADPH reductase molecule 710, as shown on the left side of FIG. 7A, its corresponding linker molecule is labeled 721. Each linker molecule can be constructed, for example, from the cofactor Flavin Mono-Nucleotide (FMN).

When activated, the NADPH reductase removes high-energy electrons from NADPH (already available inside any cell, as a source of energy), converting it into NADP+. At the level of each individual NADPH reductase molecule, the released electrons are first available at the molecule's FAD cofactor, at a location that is relatively interior to the NADPH reductase molecule. From the FAD, the electrons are transferred to the FMN linker molecule, which then carries the electrons to the anode. That is why, for linker molecule 721, it is shown as connecting to a relatively interior point of NADPH reductase molecule 710 (that interior location is indicated as "electron transfer" point 723). From the anode, the electrons are available as an electric current, in order to power the IMD.

In the above-described electron transfer process, however, the transfer from the FAD to the FMN only occurs if the NADPH reductase is activated. Calcium ions activate the NADPH reductase by binding to its calmodulin, thereby causing a conformational shift in the structure of the NADPH reductase.

Calcium ions, however, cannot bind to calmodulin at normal intracellular levels of calcium ion concentration. A neuron's soma only reaches a sufficiently high calcium ion concentration when it is strongly-activated. In particular, during the time when a neuron's polarization is decreasing, and it is preparing to produce a next strong-activation pulse, the requisite calcium ion concentration is only reached at, or shortly before, the point in time when depolarization is sufficient to cause the neuron to "fire" (i.e., produce an action potential). Thus, the calmodulin acts as a kind of calcium concentration monitoring element. When the threshold concentration is reached, the calmodulin acts as a switching element, turning on the electron flow. Once the NADPH reductase has been activated, as discussed above, the NADPH to NADP+ oxidation reaction produces about −0.4 volts.

Binding each linker molecule to the anode (e.g., binding the lower portion of linker molecule 721 to the anode, as depicted on the left side of FIG. 7A), can be accomplished by a photochemical bond (e.g., photochemical bond 722, as indicated on the left side of FIG. 7A). Such photochemical bonding is accomplished at an earlier stage of IMD manufacture.

Figure 7B:
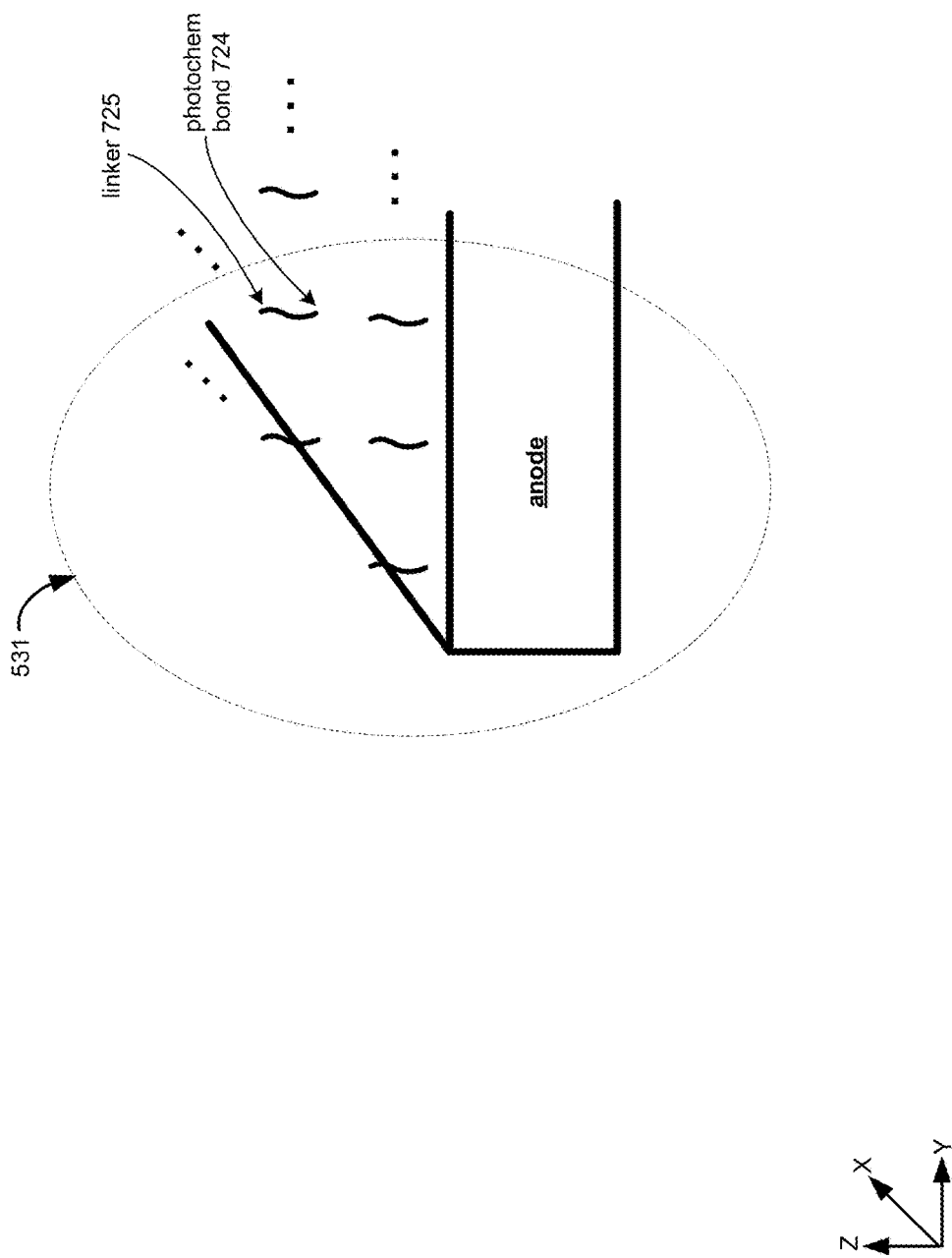
FIG. 7B shows the same highly magnified view of region 531 as is shown in FIG. 7A, but at an earlier point in the manufacturing process, when only be linker molecules are attached.

Such earlier stage is shown in FIG. 7B. In that earlier stage, the entire IMD can first be coated with a photochemical bonding material, over which linker (e.g., FMN) molecules are applied. Where the IMD is subjected to illumination, the photochemical bonding material attaches linker molecules to the metal layer. Illumination is restricted to only the surface of metal layer 525, such that the FMN linker is attached only to the IMD's anode. Once the linker molecules are attached, the residual photochemical bonding material, and the residual linker, can be removed.

The result is shown in FIG. 7B, where there is simply, at this stage in the IMD manufacture process, only linker molecules bonded to the anode (as an example, FIG. 7B points to a linker molecule 725, attached to the anode by photochemical bond 724). We shall refer to IMD's, at this stage of manufacturing, as FMN-treated IMD's. The FMN-treated IMD's, and the NADPH reductase, can be combined in a common solution. After the NADPH reductase molecules have attached to the linker molecules of the IMD's, excess NADPH reductase, as well as excess FAD, can be removed with chromatography techniques.

Prior to combining the NADPH reductase and FMN-treated IMD's, the NADPH reductase is (as mentioned above) combined with the FAD. Excess FAD can be removed with chromatography techniques. During this step, some FAD may attach at NADPH reductase sites that are (if FMN were present) more strongly compatible with FMN. When the NADPH reductase is combined with the FMN-treated IMD's (the step described in the previous paragraph), many such FAD molecules can be displaced, causing at least some of the excess FAD described above.

8.4.2.2 Cathode

For the IMD design, as shown in view 505 of FIG. 5B, a corner region 532, of layers 526 and 527, is indicated. Region 532 is shown in magnified form in FIG. 8A. Like FIG. 5B, FIG. 8A continues to show layer 526 as a homogeneous metal layer (labeled "cathode" in FIG. 8A). The increased magnification of FIG. 8A, however, permits layer 527 to be shown quite differently.

Figure 8A:
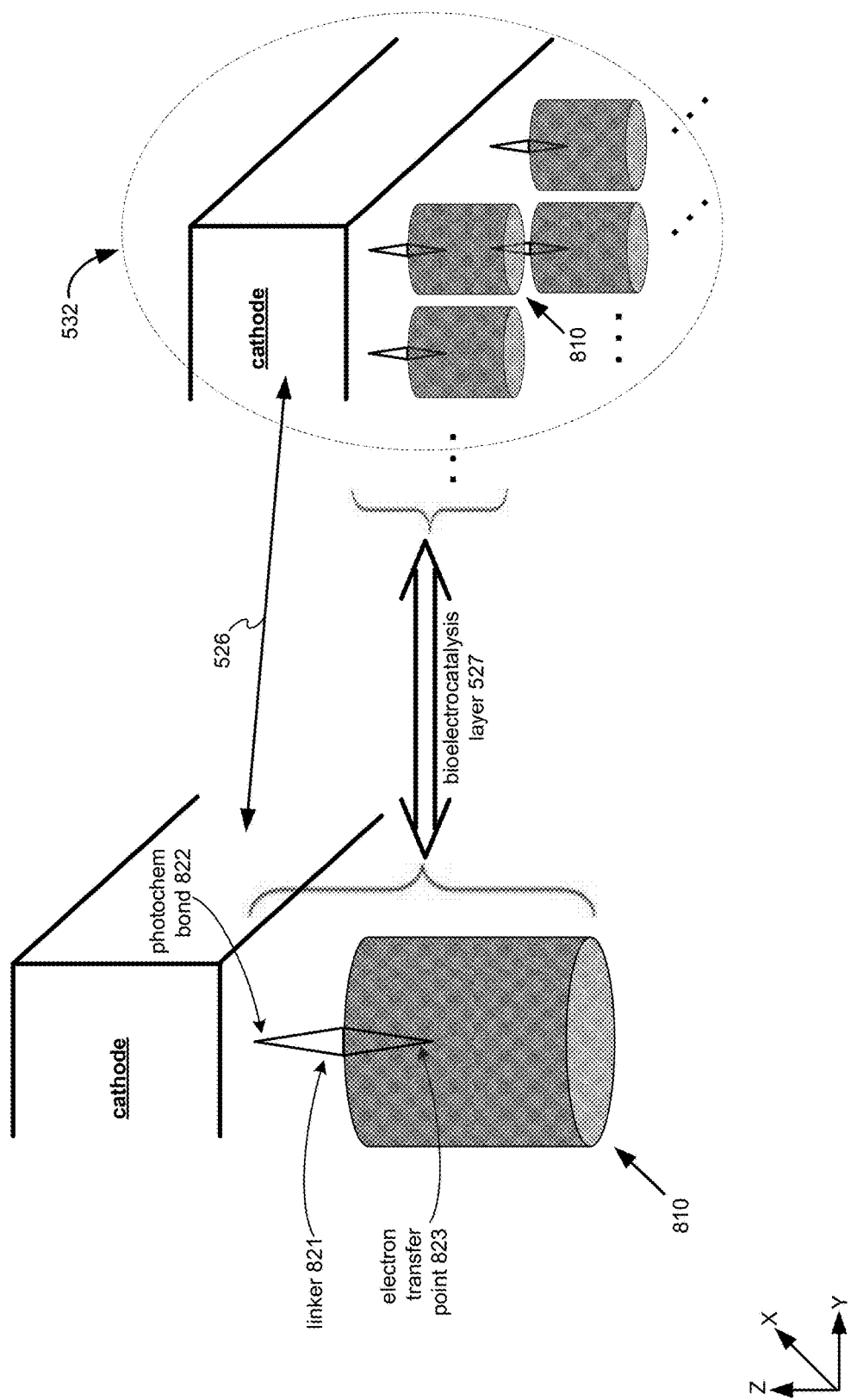
FIG. 8A is a highly magnified view of region 532, as indicated in FIG. 5B, that shows individual catalyst and linker molecules.

Layer 527 is composed primarily of relatively large and complex laccase molecules (the enzyme). Each laccase molecule, of FIG. 8A, is represented in greatly simplified form as a cylindrical shape, rather than as a ribbon diagram. For each laccase molecule, only its outer perimeter is indicated, in a first-order approximate way, by the cylindrical outline. As shown on the right side of FIG. 8A, region 532 encloses four laccase molecules, one of which is labeled 810. The left side of FIG. 8A focuses just upon laccase molecule 810.

In addition to the laccase molecules, layer 527 is also shown as including linker molecules. For each laccase molecule, it is anchored to the anode by a corresponding linker molecule. For example laccase molecule 810, as shown on the left side of FIG. 8A, its corresponding linker molecule is labeled 821.

In order to be active, the laccase depends upon a supply of electrons from the cathode (produced by the above-described NADPH reductase). If active, the laccase converts oxygen to water (i.e., converts $O_2$ to $H_2O$). As described above, this reduction reaction produces an electric current at about +0.8 volts. To provide electrons in a way that the laccase can use, the electrons need to be made available at a location that is relatively interior to the laccase molecule. That is why, for linker molecule 821, it is shown as connecting to a relatively interior point of laccase molecule 810 (that interior location is indicated as "electron transfer" point 823).

Each linker molecule can be constructed, for example, from osmium tetroxide ($OsO_4$).

Figure 8B:
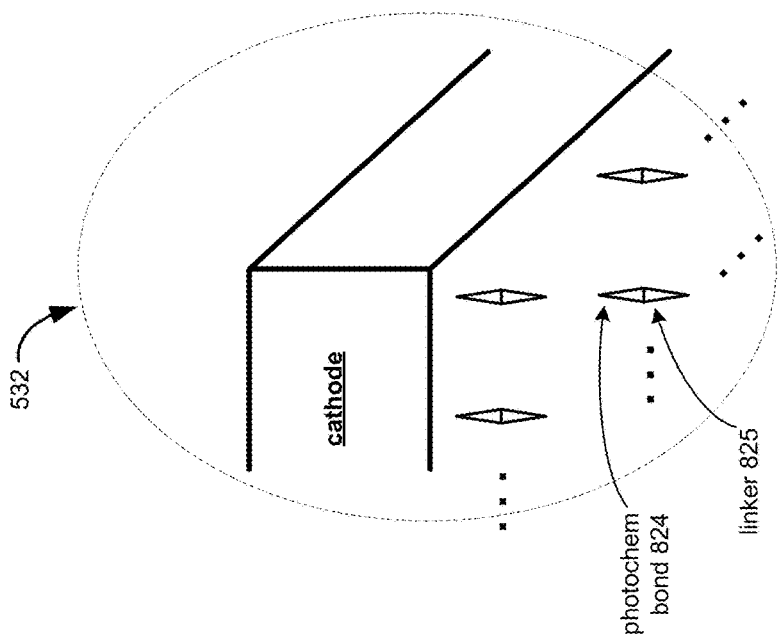
FIG. 8B shows the same highly magnified view of region 532 as is shown in FIG. 8A, but at an earlier point in the manufacturing process, when only be linker molecules are attached.

Binding each linker molecule to the cathode (e.g., binding the upper portion of linker molecule 821 to the cathode, as depicted on the left side of FIG. 8A), can be accomplished by a photochemical bond (e.g., photochemical bond 822, as indicated on the left side of FIG. 8A). Such photochemical bonding is accomplished in an earlier stage of IMD manufacture. Such earlier stage is shown in FIG. 8B. In that earlier stage, the entire IMD can first be coated with a photochemical bonding material, over which linker molecules are applied. Where the IMD is subjected to illumination, the photochemical bonding material attaches linker molecules to the metal layer. Illumination is restricted to only the surface of metal layer 526, such that the osmium tetroxide linker is attached only to the cathode.

Once the linker molecules are attached, the residual photochemical bonding material, and the residual linker, can be removed. The result is shown in FIG. 8B, where there is simply, at this stage in the IMD manufacture process, only linker molecules bonded to the cathode (as an example, FIG. 8B points to a linker molecule 825, attached to the cathode by photochemical bond 824).

When the laccase and the osmium-tetroxide-treated IMD's are combined in a common solution, a single laccase molecule binds to each linker molecule of the cathode, and to no other surface of the IMD, resulting in a cathode surface as is shown on the right side of FIG. 8A. Excess laccase can be removed by chromatography techniques. Laccase is available from such companies as MetGen Oy (Kaarina, Finland).

8.5 Endocytosis

Thus far, the path of an IMD, to the inside a cell body, has been described up to the point where an IMD comes into contact with the exterior of the cell membrane. For example, with respect to FIG. 4A, an IMD 420 is depicted as about to contact the exterior wall of one of the somas that form the cubic region of cells labeled 413.

Figure 9:
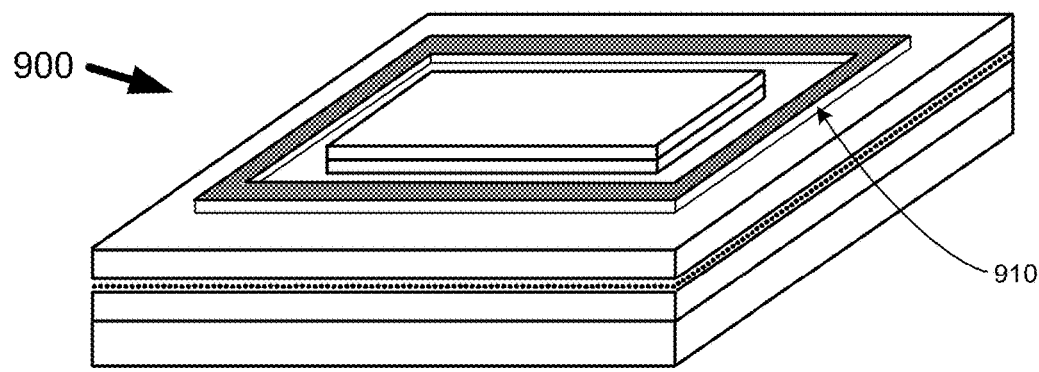
FIG. 9 depicts an example peptide-coating technique, for the IMD structure discussed above with respect to FIG. 5A.
Figure 9:
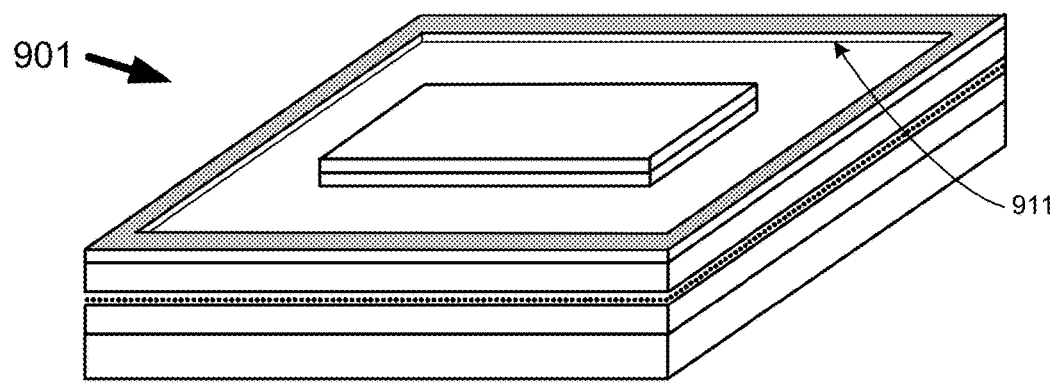
Figure 9:
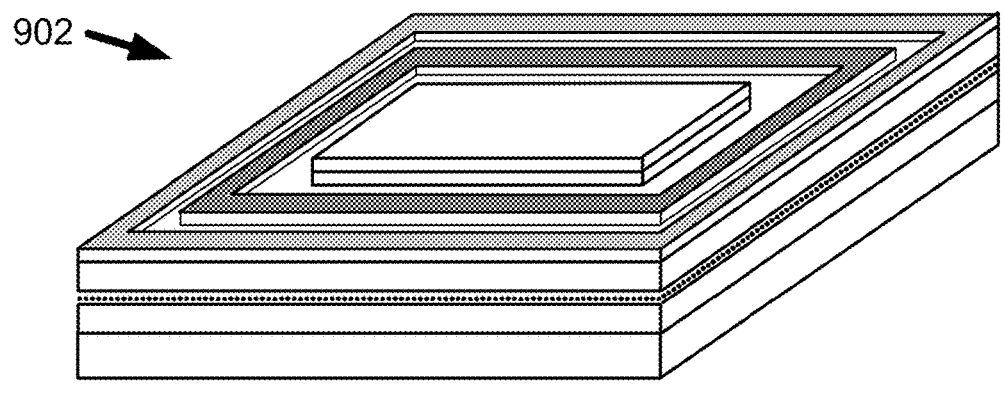
Figure 9:
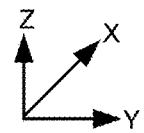

As has been mentioned above, entry of an IMD into a cell body can be accomplished by endocytosis. A peptide coating can be added to an IMD such that, once the IMD is in contact with a cell wall, endocytosis is induced. FIG. 9 depicts an example peptide-coating technique, for the IMD structure discussed above with respect to FIG. 5A.

FIG. 9 has three views, labeled 900-902, each of which shows an IMD from the same perspective as is shown in view 500 of FIG. 5A. The difference between views 900-902, and view 500, is the presence of one or more rings of a peptide, around the anode and bioelectrocatalysis layers (layers 525 and 524). Specifically, view 900 depicts an IMD with a single peptide ring 910, while view 901 depicts another single peptide ring labeled 911. View 902 depicts an IMD with both peptide ring 910 and peptide ring 911. Peptide ring 910 can be composed of any amphiphilic peptide, suitable for endosome release, such as the "Palm 1" peptide. For example, see the following publication, herein incorporated by reference in its entirety:

"Nanoparticle targeting to neurons in a rat hippocampal slice culture model," by Walters et al., in ASN Neuro (American Society for Neurochemistry), Volume 4, September 2012, pages 383-392.

Peptide ring 911 can be composed of any suitable cell permeable peptide, such as the "Tat" peptide. For example, see the following publication, herein incorporated by reference in its entirety:

"Different mechanisms for cellular internalization of the HIV-1 Tat-derived cell penetrating peptide and recombinant proteins fused to Tat," by Silhol et al., in European Journal of Biochemistry, Volume 269, January 2002, pages 494-501.

The peptide rings need be applied to only one side of an IMD. For purposes of example, FIG. 9 shows the rings around the anode side of an IMD, but the same rings could be applied, instead, to the cathode side (i.e., the side visible in view 501 of FIG. 5A). The peptide coating, forming each of the rings, typically has a depth of only about one peptide molecule. Attachment of the peptide molecules can be accomplished using a similar method to that described above, for anchoring a bioelectrocatalysis enzyme molecule with a photochemically-bonded linker molecule. For each of the peptides to be used, an appropriate linker molecule can be attached to the IMD surface (i.e., to either the N-type layer 521 or substrate 520), by use of photochemical bonding. When a peptide is applied to the IMD's surface, its molecules only attach (covalently) at those locations where the corresponding linker molecule has been bonded.

8.6 Inert Coating

Except for bioelectrocatalysis layers 524 and 527, each IMD can be coated with a material that has at least the following two properties:

- it does not interact with the normal biological processes of the cell in which the IMD is implanted (i.e., the coating is biologically inert); and
- it is transparent to the EM radiation (e.g., NIR) transmitted by an IMD.

An example coating material, that satisfies these two properties, is the Parylene family of compounds, and, in particular, Parylene-C.

Once an IMD has been coated, the peptide rings for inducing endocytosis (discussed in the previous section) can be added.

9 Computing Equipment

In accordance with what is ordinarily known by those in the art, the DSP described herein (e.g., DSP 1160) contains computational hardware (e.g., integrated circuits), and programmable memories (volatile and/or non-volatile), of various types.

Computational hardware, whether in integrated circuit form or otherwise, is typically based upon the use of transistors (field effect and/or bipolar), although other types of components (e.g., optical, microelectromechanical, or magnetic) may be included. Any computational hardware has the property that it will consume energy, as a necessary part of being able to perform its function. Also, regardless of how quickly it can be made to operate, computational hardware will require some amount of time to change state. Because of its basis on physical devices (electronic or otherwise), computational hardware, however small, will occupy some amount of physical space.

Programmable memories are also often implemented in integrated circuit form, and are subject to the same physical limitations described above for computational hardware. A programmable memory is intended to include devices that use any kind of physics-based effects or properties, in order to store information in at least a non-transitory way, and for an amount of time commensurate with the application. The types of physical effects used to implement such storage, include, but are not limited to: maintenance of a particular state through a feedback signal, charge storage, changes to optical properties of a material, magnetic changes, or chemical changes (reversible or irreversible).

Unless specifically indicated otherwise, the terms computational hardware, programmable memory, computer-readable media, system, and sub-system, do not include persons, or the mental steps a person may undertake.

The kind of information described herein (such as data and/or instructions), that is on computer-readable media and/or programmable memories, can be stored on computer-readable code devices embodied therein. A computer-readable code device can represent that portion of a memory in which a defined unit of information (such as a bit) can be stored and/or from which a defined unit of information can be retrieved.

10 Glossary of Selected Terms biochemical substance: Any chemical substance that is a part of, or a result of, the processes of living organisms.

bioelectrocatalysis: The use of biological materials to produce oxidation and reduction reactions, resulting in electron transfer. This typically involves the use of specific enzymes. The result, of producing bioelectrocatalysis, is an electric current that can be used to power an electric circuit.

capsid protein: The protein shell of a virus.

cell: Unless the context specifically indicates otherwise, any use of the term "cell" herein is a reference to the basic biological unit of living organisms. This basic biological unit is enclosed within a cell membrane, the membrane enclosing (at least) the cell's cytoplasm, nucleus, and organelles.

cerebral cortex: the outermost layer of neural tissue, for a mammalian brain.

EM: Electromagnetic.

endocytosis: The process by which a cell absorbs material, initially external to its cell membrane, by engulfing the material.

IMD: an Intracellular Monitoring Device, for implantation within a living cell, that includes at least some microelectronics, and that is small enough such that it causes no significant impairment to its enclosing cell's biological processes. The IMD also includes a transmitter that can transmit data it has collected to a receiver (or antenna) located external to its enclosing cell.

"Large Scale Fine Grained" (LSFG) neural monitoring: Across a volume of cortical-matter large enough to include, at least, thousands of active neurons, an ability to individually monitor the activity of a large number of those neurons (e.g., at least hundreds of neurons).

NCL: Nano-Collimating Lens.

NIR: Near Infrared. As used herein, NIR refers to a region, of the EM spectrum, just below the visual spectrum for humans (hence the "nearness" of NIR), but is still above lower-frequency ranges of infrared, such as Short-Wavelength Infrared (or SWIR). More specifically, the NIR referred-to herein is typically in the wavelength range of approximately 700 μm to 1100 μm.

nm: Nanometer, or $1.0 \times 10^{-9}$ meters.

QD: Quantum Dot.

QD-LED: Quantum Dot Light Emitting Device.

rat: The "laboratory rat" (or simply "rat"), as described herein, refers to any one of the commonly and commercially available species of the *Rattus norvegicus*, that has been bred for scientific research. This includes, for example, the Long-Evans laboratory rat.

μm: Micrometer (or just micron), is $1.0 \times 10^{-6}$ meters.

While the invention has been described in conjunction with specific embodiments it is evident that many alternatives, modifications and variations will be apparent in light of the foregoing description. Accordingly, the invention is intended to embrace all such alternatives, modifications and variations, as well as those equivalents that fall within the spirit and scope of this description and its appended claims.

What is claimed is:

1. A system for monitoring intracellular activity, comprising:
    a first intracellular monitoring device that includes a first semiconductor substrate, wherein the first intracellular monitoring device is located completely inside a first cell, and a longest dimension, of the first substrate, is no more than approximately one micrometer;
    a first P-type layer, manufactured on the first semiconductor substrate;
    a first N-type layer, manufactured on the first semiconductor substrate;
    a first quantum dot layer, manufactured on the first semiconductor substrate, and located between the first P-type layer and first N-type layer, wherein a first level of electric current, at a first voltage, when present, is sufficient to cause the first quantum dot layer to emit near infrared electromagnetic radiation that includes at least a first frequency;
    a first metal layer, manufactured on the first semiconductor substrate, wherein a first side of the first metal layer is in electrical contact with the first N-type layer, and a second side of the first metal layer faces the cytoplasm of the first cell;

a second metal layer, manufactured on the first semiconductor substrate, wherein a first side of the second metal layer is in electrical contact with the first P-type layer, and a second side of the second metal layer faces the cytoplasm of the first cell;

a first enzyme layer, coating the second side of the first metal layer with a first enzyme, wherein the first enzyme is activated, to produce electrons, by a first concentration of a first biochemical substance, within the cytoplasm of the first cell, that is at least a first threshold level;

a second enzyme layer, coating the second side of the second metal layer with a second enzyme, wherein the electrons produced by the first enzyme layer form at least the first electric current level, and at least part of the first voltage, when they are received by, and activate, the second enzyme layer;

a first antenna, located outside the first cell, that collects near infrared from a plurality of intracellular monitoring devices, wherein a first portion of near infrared collected is from the first quantum dot layer; and an optical domain frequency analyzer, coupled to the first antenna, that detects, at least, a presence of the first frequency in the near infrared collected by the first antenna in order to produce a first frequency specific output.

2. The system of claim 1, wherein the first cell is a first neuron, the first biochemical substance is a calcium ion, and the first concentration is a calcium ion concentration within the first cell.

3. The system of claim 2, wherein the first concentration reaching at least the first threshold level is indicative of the first neuron generating a strong action potential.

4. The system of claim 1, further comprising:
a first coating of a peptide, on a first exterior surface of the first intracellular monitoring device, wherein the first coating permits the first intracellular monitoring device, when in contact with an outer membrane of a cell, to induce endocytosis and completely enter a cell.

5. The system of claim 4, wherein the first peptide, after the intracellular monitoring device has entered the first cell, is digestable.

6. The system of claim 1, further comprising:
wherein the electrons produced by the first enzyme layer form at least the first electric current, and at least the first voltage, when they are received by, and activate, the second enzyme layer.

7. The system of claim 1, further comprising:
a second intracellular monitoring device that includes a second semiconductor substrate, wherein the second intracellular monitoring device is located completely inside a second cell, and a longest dimension, of the second substrate, is no more than approximately one micrometer;

a second P-type layer, manufactured on the second semiconductor substrate;

a second N-type layer, manufactured on the second semiconductor substrate;

a second quantum dot layer, manufactured on the second semiconductor substrate, and located between the second P-type layer and second N-type layer, wherein the first level of electric current, at the first voltage, when present, is sufficient to cause the second quantum dot layer to emit near infrared electromagnetic radiation that includes at least a second frequency;

a third metal layer, manufactured on the second semiconductor substrate, wherein a first side of the third metal layer is in electrical contact with the second N-type layer, and a second side of the third metal layer faces the cytoplasm of the second cell;

a fourth metal layer, manufactured on the second semiconductor substrate, wherein a first side of the fourth metal layer is in electrical contact with the second P-type layer, and a second side of the fourth metal layer faces the cytoplasm of the second cell;

a third enzyme layer, coating the second side of the third metal layer with the first enzyme, wherein the first enzyme is activated, to produce electrons, by the first concentration of the first biochemical substance, within the cytoplasm of the second cell, that is at least the first threshold level;

a fourth enzyme layer, coating the second side of the fourth metal layer with the second enzyme, wherein the electrons produced by the third enzyme layer form at least part of the first electric current level, and at least part of the first voltage, when they are received by, and activate, the fourth enzyme layer;

wherein the first antenna is located outside the second cell;

wherein a second portion, of near infrared collected by the first antenna, is from the second quantum dot layer; and wherein the optical domain frequency analyzer, coupled to the first antenna, detects, at least, a presence of the second frequency in the near infrared collected by the first antenna in order to produce a second frequency specific output.

8. The system of claim 7, further comprising:
a sub-system, including a photodetector, and a digital signal processor configured with programmable memory, that converts the first frequency specific output into a first digital pulse stream, representative of data captured by the first intracellular monitoring device; and a sub-system, including a photodetector, and a digital signal processor configured with programmable memory, that converts the second frequency specific output into a second digital pulse stream, representative of data captured by the second intracellular monitoring device.

* * * * *